(12) United States Patent
Mirkin et al.

(10) Patent No.: US 7,115,688 B1
(45) Date of Patent: Oct. 3, 2006

(54) NANOPARTICLES WITH POLYMER SHELLS

(75) Inventors: Chad A. Mirkin, Wilmette, IL (US); SonBinh T. Nguyen, Evanston, IL (US)

(73) Assignee: Nanosphere, Inc., Northbrook, IL (US)

( * ) Notice: Subject to any disclaimer, the term of this patent is extended or adjusted under 35 U.S.C. 154(b) by 0 days.

(21) Appl. No.: 09/830,620

(22) PCT Filed: Nov. 30, 1999

(86) PCT No.: PCT/US99/28387

§ 371 (c)(1),
(2), (4) Date: Aug. 15, 2001

(87) PCT Pub. No.: WO00/33079

PCT Pub. Date: Jun. 8, 2000

Related U.S. Application Data

(60) Provisional application No. 60/110,327, filed on Nov. 30, 1998.

(51) Int. Cl.
C08F 4/44 (2006.01)
(52) U.S. Cl. .................. 526/127; 526/161; 526/171; 526/172; 526/280; 526/281
(58) Field of Classification Search ............... 526/161, 526/171, 172, 280, 281, 127
See application file for complete search history.

(56) References Cited

U.S. PATENT DOCUMENTS

| | | |
|---|---|---|
| 4,023,981 A | 5/1977 | Perronin et al. |
| 4,193,983 A | 3/1980 | Ullman et al. |
| 4,256,834 A | 3/1981 | Zuk et al. |
| 4,261,968 A | 4/1981 | Ullman et al. |
| 4,313,734 A | 2/1982 | Leuvering |
| 4,318,707 A | 3/1982 | Litman et al. |
| 4,454,234 A | 6/1984 | Czerlinski |
| 4,650,770 A | 3/1987 | Liu et al. |
| 4,713,348 A | 12/1987 | Ullman |
| 4,846,893 A | 7/1989 | Akasaki et al. |
| 4,853,335 A | 8/1989 | Olsen et al. |
| 4,868,104 A | 9/1989 | Kurn et al. |
| 4,996,143 A | 2/1991 | Heller et al. .................... 435/6 |
| 5,053,471 A | 10/1991 | Goto et al. |
| 5,225,064 A | 7/1993 | Henkens et al. |
| 5,284,748 A | 2/1994 | Mroczkowski et al. |
| 5,288,609 A | 2/1994 | Engelhardt et al. |
| 5,294,369 A | 3/1994 | Shigekawa et al. |
| 5,312,940 A | 5/1994 | Grubbs et al. .............. 556/136 |
| 5,342,909 A | 8/1994 | Grubbs et al. .............. 526/171 |
| 5,360,895 A | 11/1994 | Hainfeld et al. |
| 5,384,073 A | 1/1995 | Shigekawa et al. |
| 5,384,265 A | 1/1995 | Kidwell et al. |
| 5,460,831 A | 10/1995 | Kossovsky et al. |
| 5,468,819 A | 11/1995 | Goodall et al. .............. 526/171 |
| 5,472,881 A | 12/1995 | Beebe et al. |
| 5,508,164 A | 4/1996 | Kausch et al. ................. 435/6 |
| 5,514,602 A | 5/1996 | Brooks, Jr. et al. |
| 5,521,289 A | 5/1996 | Hainfeld et al. |
| 5,543,158 A | 8/1996 | Gref et al. |
| 5,569,730 A | 10/1996 | Goodall et al. .............. 526/282 |
| 5,571,726 A | 11/1996 | Brooks, Jr. et al. |
| 5,571,881 A | 11/1996 | Goodall et al. .............. 526/171 |
| 5,599,668 A | 2/1997 | Stimpson et al. |
| 5,606,085 A | 2/1997 | Bell et al. ....................... 556/57 |
| 5,609,907 A | 3/1997 | Natan ......................... 427/2.12 |
| 5,637,508 A | 6/1997 | Kidwell et al. |
| 5,639,620 A | 6/1997 | Siiman et al. |
| 5,639,900 A | 6/1997 | Bell et al. ....................... 556/57 |
| 5,641,515 A | 6/1997 | Ramtoola ................... 424/189 |

(Continued)

FOREIGN PATENT DOCUMENTS

EP    0 630 974 A2    6/1994

(Continued)

OTHER PUBLICATIONS

Stimpson, et al., "Real-time detection of DNA hybridization and melting on oligonucleotide arrays by using optical wave guides," *Proc. Natl. Acad. Sci..*, vol. 92, pp. 6379-6383, California Institute of Technology (1995) U.S.

(Continued)

*Primary Examiner*—Robert D. Harlan
(74) *Attorney, Agent, or Firm*—McDonnell Boehnen Hulbert & Berghoff LLP

(57) ABSTRACT

The invention provides a method of preparing nanoparticles having at least one polymer shell attached to them, each polymer shell having a selected property or properties. The method comprises attaching initiation monomers to the surfaces of the nanoparticles, contacting the nanoparticles having the initiation monomers attached to them with a transition metal ring-opening metathesis catalyst to activate the initiation monomers, and contacting the nanoparticles with one or more types of propagation monomers of the formula P—L—N under conditions effective so that the monomers are polymerized to form the one or more polymer shells. In the formula P—L—N, N is a cyclic olefin-containing group, P is a moiety which gives each polymer shell a selected property or properties, and L is a bond or linker. The invention also provides polymers formed by polymerizing the propagation monomers. The invention further provides the nanoparticles, the initiation monomers, and propagation monomers of formula P—L—N wherein P is a moiety having a property selected from the group consisting of redox activity, optical activity, electrical activity and magnetic activity, and L and N are defined above. The invention also provides binding monomers of formula B—L—N, wherein B is a binding moiety that binds specifically to an analyte, and N and L are defined above. Finally, the invention provides methods and kits for detecting or quantitating an analyte.

44 Claims, 12 Drawing Sheets

U.S. PATENT DOCUMENTS

| | | |
|---|---|---|
| 5,665,582 A | 9/1997 | Kaushch et al. |
| 5,677,405 A | 10/1997 | Goodall et al. .............. 526/281 |
| 5,681,943 A | 10/1997 | Letsinger et al. |
| 5,705,196 A | 1/1998 | Galan Valdivia et al. ... 424/497 |
| 5,710,298 A | 1/1998 | Grubbs et al. ................. 556/22 |
| 5,728,785 A | 3/1998 | Grubbs et al. ............... 526/142 |
| 5,728,917 A | 3/1998 | Grubbs et al. ............... 585/653 |
| 5,731,383 A | 3/1998 | Nubel et al. ................. 525/297 |
| 5,736,413 A | 4/1998 | Uzan et al. |
| 5,741,869 A | 4/1998 | Goodall et al. .............. 526/171 |
| 5,747,248 A | 5/1998 | Collins |
| 5,750,815 A | 5/1998 | Grubbs et al. ............... 585/511 |
| 5,751,018 A | 5/1998 | Alivisatos et al. |
| 5,766,764 A | 6/1998 | Olli et al. |
| 5,780,565 A | 7/1998 | Clough et al. ............... 526/206 |
| 5,808,126 A | 9/1998 | Brzezinska et al. .......... 556/431 |
| 5,811,515 A | 9/1998 | Grubbs et al. ............... 530/330 |
| 5,830,986 A | 11/1998 | Merrill et al. ............... 528/332 |
| 5,831,108 A | 11/1998 | Grubbs et al. ................. 556/21 |
| 5,837,859 A | 11/1998 | Teoule et al. ............... 536/25.3 |
| 5,840,820 A | 11/1998 | DeSimone et al. .......... 526/169 |
| 5,849,851 A | 12/1998 | Grubbs et al. ................. 526/93 |
| 5,880,231 A | 3/1999 | Grubbs et al. ............... 526/171 |
| 5,900,481 A | 5/1999 | Lough et al. ............... 536/55.3 |
| 5,916,983 A | 6/1999 | Pederson et al. ........... 526/170 |
| 5,917,071 A | 6/1999 | Grubbs et al. ................. 556/21 |
| 5,922,537 A | 7/1999 | Ewart et al. .................... 435/6 |
| 5,922,863 A | 7/1999 | Grubbs et al. ............... 540/538 |
| 5,939,021 A | 8/1999 | Hansen et al. |
| 5,939,504 A | 8/1999 | Woodson, Jr. et al. ...... 526/145 |
| 5,969,170 A | 10/1999 | Grubbs et al. ................. 556/21 |
| 5,972,615 A | 10/1999 | An et al. ......................... 435/6 |
| 5,990,479 A | 11/1999 | Weiss et al. |
| 6,020,443 A | 2/2000 | Woodson et al. ........... 526/135 |
| 6,025,202 A | 2/2000 | Natan |
| 6,040,363 A | 3/2000 | Warner et al. ............... 523/214 |
| 6,048,993 A | 5/2000 | Grubbs et al. ................. 556/21 |
| 6,060,570 A | 5/2000 | Nubel et al. ................. 526/308 |
| 6,071,459 A | 6/2000 | Warner et al. ............... 264/311 |
| 6,080,826 A | 6/2000 | Grubbs et al. ................. 526/75 |
| 6,107,237 A | 8/2000 | Wagener et al. ............ 502/240 |
| 6,107,420 A | 8/2000 | Grubbs et al. ................. 526/73 |
| 6,111,121 A | 8/2000 | Grubbs et al. ................. 556/21 |
| 6,121,473 A | 9/2000 | Schrock et al. ................ 556/57 |
| 6,143,211 A * | 11/2000 | Mathiowitz et al. ........... 264/4 |
| 6,143,851 A | 11/2000 | Nubel et al. ................. 526/308 |
| 6,149,868 A | 11/2000 | Natan |
| 6,156,692 A | 12/2000 | Nubel et al. ................. 502/155 |
| 6,159,890 A | 12/2000 | Nubel et al. ................. 502/155 |
| 6,160,103 A | 12/2000 | Marchand et al. .......... 536/23.1 |
| 6,203,989 B1 | 3/2001 | Goldberg et al. .............. 435/6 |
| 6,211,391 B1 | 4/2001 | Grubbs et al. ................. 556/21 |
| 6,214,560 B1 | 4/2001 | Yguerabide et al. ......... 435/7.1 |
| 6,225,488 B1 | 5/2001 | Mukarjee et al. ............. 556/22 |
| 6,232,482 B1 | 5/2001 | Schwab et al. ................ 556/21 |
| 6,251,303 B1 | 6/2001 | Bawendi et al. ....... 252/301.4 R |
| 6,264,825 B1 | 7/2001 | Blackburn et al. ........ 205/777.5 |
| 6,271,315 B1 | 8/2001 | Kiessling et al. ......... 525/326.1 |
| 6,277,489 B1 | 8/2001 | Abbott et al. ................ 428/403 |
| 6,284,852 B1 | 9/2001 | Lynn et al. .................. 526/171 |
| 6,288,197 B1 | 9/2001 | Youngs et al. ................. 528/25 |
| 6,291,616 B1 | 9/2001 | Kiessling et al. ............ 526/171 |
| 6,306,610 B1 | 10/2001 | Bawendi et al. ............. 435/7.1 |
| 6,310,121 B1 | 10/2001 | Woodson, Jr. et al. ........ 524/32 |
| 6,323,296 B1 | 11/2001 | Warner et al. ............... 526/171 |
| 6,342,621 B1 | 1/2002 | Mukerjee et al. .............. 556/21 |
| 6,346,652 B1 | 2/2002 | Schrock et al. ............. 585/643 |
| 6,348,551 B1 | 2/2002 | Fürstner et al. ............. 526/171 |
| 6,361,944 B1 | 3/2002 | Mirkin et al. .................... 435/6 |
| 6,365,418 B1 | 4/2002 | Wagner et al. ............... 436/518 |
| 6,417,340 B1 | 7/2002 | Mirkin et al. ............... 536/23.1 |
| 6,495,324 B1 | 12/2002 | Mirkin et al. .................... 435/6 |
| 6,506,564 B1 | 1/2003 | Mirkin et al. .................... 435/6 |
| 6,509,459 B1 | 1/2003 | Agrawal et al. |
| 6,582,921 B1 | 6/2003 | Mirkin et al. .................... 435/6 |
| 6,602,669 B1 | 8/2003 | Mirkin et al. .................... 435/6 |
| 6,610,491 B1 | 8/2003 | Mirkin et al. .................... 435/6 |
| 6,645,721 B1 | 11/2003 | Mirkin et al. .................... 435/6 |
| 6,673,548 B1 | 1/2004 | Mirkin et al. .................... 435/6 |
| 6,677,122 B1 | 1/2004 | Mirkin et al. .................... 435/6 |
| 6,682,895 B1 | 1/2004 | Mirkin et al. .................... 435/6 |
| 6,709,825 B1 | 3/2004 | Mirkin et al. .................... 435/6 |
| 6,720,147 B1 | 4/2004 | Mirkin et al. .................... 435/6 |
| 6,720,411 B1 | 4/2004 | Mirkin et al. ............... 536/23.1 |
| 6,726,847 B1 | 4/2004 | Mirkin et al. ................... 216/90 |
| 6,730,269 B1 | 5/2004 | Mirkin et al. ............... 422/68.1 |
| 6,740,491 B1 | 5/2004 | Mirkin et al. .................... 435/6 |
| 6,750,016 B1 | 6/2004 | Mirkin et al. .................... 435/6 |
| 6,759,199 B1 | 7/2004 | Mirkin et al. .................... 435/6 |
| 6,767,702 B1 | 7/2004 | Mirkin et al. .................... 435/6 |
| 6,773,884 B1 | 8/2004 | Mirkin et al. .................... 435/6 |
| 6,777,186 B1 | 8/2004 | Mirkin et al. .................... 435/6 |
| 2002/0137070 A1 | 9/2002 | Mirkin et al. .................... 435/6 |
| 2002/0155461 A1 | 10/2002 | Mirkin et al. .................... 435/6 |
| 2002/0160381 A1 | 10/2002 | Mirkin et al. .................... 435/6 |
| 2002/0177143 A1 | 11/2002 | Mirkin et al. .................... 435/6 |
| 2002/0192687 A1 | 12/2002 | Mirkin et al. .................... 435/6 |
| 2003/0054358 A1 | 3/2003 | Mirkin et al. .................... 435/6 |
| 2003/0068622 A1 | 4/2003 | Mirkin et al. .................... 435/6 |
| 2003/0068638 A1 | 4/2003 | Mirkin et al. .................... 435/6 |
| 2003/0087242 A1 | 5/2003 | Mirkin et al. .................... 435/6 |
| 2003/0113740 A1 | 6/2003 | Mirkin et al. .................... 435/6 |
| 2003/0124528 A1 | 7/2003 | Mirkin et al. .................... 435/6 |
| 2003/0129608 A1 | 7/2003 | Mirkin et al. .................... 435/6 |
| 2003/0143538 A1 | 7/2003 | Mirkin et al. .................... 435/6 |
| 2003/0143598 A1 | 7/2003 | Mirkin et al. .................... 435/6 |
| 2003/0148282 A1 | 8/2003 | Mirkin et al. .................... 435/6 |
| 2003/0207296 A1 | 11/2003 | Mirkin et al. .................... 435/6 |
| 2003/0211488 A1 | 11/2003 | Mirkin et al. .................... 435/6 |
| 2004/0038255 A1 | 2/2004 | Mirkin et al. .................... 435/6 |
| 2004/0053222 A1 | 3/2004 | Mirkin et al. .................... 435/6 |
| 2004/0072231 A1 | 4/2004 | Mirkin et al. .................... 435/6 |
| 2004/0086897 A1 | 5/2004 | Mirkin et al. .................... 435/6 |
| 2004/0101889 A1 | 5/2004 | Mirkin et al. .................... 435/6 |

FOREIGN PATENT DOCUMENTS

| | | |
|---|---|---|
| EP | 0 667 398 A2 | 8/1995 |
| JP | 231556 | 8/2001 |
| WO | WO 89/06801 | 7/1989 |
| WO | WO 90/02205 | 3/1990 |
| WO | WO 92/04469 | 3/1992 |
| WO | WO 93/10564 | 5/1993 |
| WO | WO 93/25709 | 12/1993 |
| WO | WO 94/29484 | 12/1994 |
| WO | WO 97/00995 | 1/1997 |
| WO | WO 97/40181 | 10/1997 |
| WO | WO 97/04740 A1 | 2/1998 |
| WO | WO 98/04740 | 2/1998 |
| WO | WO 98/10289 | 3/1998 |
| WO | WO 98/17317 | 4/1998 |
| WO | WO 98/28368 | 7/1998 |
| WO | WO 99/23258 | 10/1998 |
| WO | WO 99/20789 | 4/1999 |
| WO | WO 99/21934 | 5/1999 |
| WO | WO 99/23258 | 5/1999 |
| WO | WO 99/60169 | 11/1999 |
| WO | WO 00/25136 | 5/2000 |
| WO | WO 00/33079 | 6/2000 |
| WO | WO 00/33079 A1 | 6/2000 |
| WO | WO 01/00876 | 1/2001 |
| WO | WO 01/00876 A1 | 1/2001 |
| WO | WO 01/51665 | 7/2001 |
| WO | WO 01/051665 A2 | 7/2001 |

| WO | WO 01/73123 | 10/2001 |
| WO | WO 01/073123 A3 | 10/2001 |
| WO | WO 01/86301 | 11/2001 |
| WO | WO 02/04681 | 1/2002 |
| WO | WO 02/004681 A3 | 1/2002 |
| WO | WO 02/18643 | 3/2002 |
| WO | WO 02/018643 A3 | 3/2002 |
| WO | WO 02/36169 | 5/2002 |
| WO | WO 00/33079 | 6/2002 |
| WO | WO 02/46472 | 6/2002 |
| WO | WO 02/46483 | 6/2002 |
| WO | WO 02/046572 A3 | 6/2002 |
| WO | WO 02/079490 A3 | 10/2002 |
| WO | WO 02/096262 A2 | 12/2002 |
| WO | WO 2003/008539 A3 | 1/2003 |
| WO | WO 2003/035829 A3 | 5/2003 |
| WO | WO 2003/081202 A3 | 10/2003 |
| WO | WO 2003/087188 A1 | 10/2003 |
| WO | WO 2003/095973 A2 | 11/2003 |
| WO | WO 2004/004647 A3 | 1/2004 |
| WO | WO 2004/053105 A2 | 6/2004 |

OTHER PUBLICATIONS

Storhoff, et al, "Strategies for Organizing Nanoparticles into Aggregate Structures and Functional Materials," *Journal of Cluster Science*, vol. 8, No. 2, pp. 179-217, Plenum Publishing Corporation (1997) U.S.

Storhoff, et al., "One-Pot Colorimetric Differentiation of Polynucleotides with Single Base Imperfections Using Gold Nanoparticle Probes," *J. Am. Chem. Soc.*, vol. 20, pp. 1961-1964, American Chemical Society (1998) U.S.

Velev, et al., "In Situ Assembly of Colloidal Particles into Miniaturized Biosensors," *Langmuir*, vol. 15, No. 11, pp. 3693-3698, American Chemical Society (1999) U.S.

Zhu, et al., "The First Raman Spectrum of an Organic Monolayer on a High-Temperature Superconductor: Direct Spectroscopic Evidence for a Chemical Interaction between an Amine and $Yba_2Cu_3O_{7-\delta}$," *J. Am. Chem. Soc.*, vol. 119, pp. 235-236, American Chemical Society (1997) U.S.

Yguerabide, et al., "Light-Scattering Submicroscopic Particles as Highly Fluorescent Analogs and Their Use as Tracer Labels in Clinical and Biological Applications," I. Theory, *Analytical Biochemistry*, vol. 262, pp. 137-156 (1998) U.S.

Yguerabide, et al., "Light-Scattering Submicroscopic Particles as Highly Fluorescent Analogs and Their Use as Tracer Labels in Clinical and Biological Applications," II. Experimental Characterization, *Analytical Biochemistry*, vol. 262 pp. 157-176 (1998) U.S.

Borman, *Chem. Eng. News*, Dec. 9, 1996, pp. 42-43 (1996).

Tomlinson et al., *Anal. Biochem*, vol. 171, pp. 217-222 (1998).

Alivisatos, A. P., et al., "Organization of 'nanocrystal molecules' using DNA," *Nature*, vol. 382, p. 609-611 (1996).

Bazin, H., et al., "Peptide and biotin-oligonucleotide-pyrrole conjugates for electrochemical addressing silicon chip," *Nucleosides Nucleotides*, vol. 18, p. 1309-1310 (1999).

Bidan, G., et al., "Electropolymerization as Versatile Route for immobilizing Biological Species onto Surfaces," *Appl. Biochem. Biotechnol.*, 89, 183-193 (2000).

Braun, E., et al., "DNA-templated assembly and electrode attachment of a conducting silver wire," *Nature*, vol. 391, p. 775-778 (1998).

Caruana, D. J., et al., "Enzyme-amplified amperometric detection og hybridization and of a single base pair mutation in an 18-base oligonucleotide on a 7-um-diameter microelectrode," *Journal of the American Chemical Society*, vol. 121, p. 769-774 (1999).

Cassell, A. M., et al., "Assembly of DNA/Fullerene Hybrid Materials," *Angewandte Chemie International Edition in English* , vol. 37, p. 1528-1531 (1998).

Davies, D.I., et al., "Addition of Thiols to some 5-Substituted Norborn-2-enes," *Journal of the Chemical Socieity, Perkin Transactions*. 1, p. 433-8 (433-8 (1973).

Elghanian, R., et al., "Selective colormetric detection of polyuncleotides based on the distance-dependent optical properties of gold nanoparticles," *Science* , vol. 277, p. 1078-1080 (1997).

Kelly, S.O., et al., "Single-base mismatch detection based on charge transduction through DNA," *Nucleic Acids Research* vol. 27, p. 4830-4837 (1999).

Korri-Youssoufi, H., et al., "Toward bioelectronics specific DNA recognition based on a oligonucleotide-functionalized polypyyrrole," *Journal of the American Society*, vol. 119, p. 7388-7389 (1997).

Livache, T.,et al., "Polypyrrole DNA chip on a silicon device: example of hepatitis C virus genotyping," *Analytical Biochemistry*, vol. 255, p. 188-194 (1998).

Livache, T., et al., "Preparation of a DNA matrix via an electrochemically directed copolymerization of pyrrole and oligonucleotides bearing a pyrrole group," *Nucleic Acids Research*, vol. 22, p. 2915-2921 (1994).

Mirkin, C. A., et al., "A DNA-based method for rationally assembling nanoparticles into macroscopic materials," *Nature*, vol. 382, p. 607-609 (1996).

Napier, M. E., et al., "Probing biomolecule recognition with electron transfer; electrochemical sensors for DNA hybridization," *Bioconjugate Chemistry*, vol. 8, p. 906-913 (1997).

Niemeyer, C. M., "Self-assembled nanostructures based on DNA: towards the development of nanobiotechnology," *Current Opinion in Chemical Biology*, vol. 4, p. 609-618 (2000).

Neimeyer, C. M., et al., "Superamolecular Nanocircles consisting of streptavidin and DNA," *Angewandte Chemie International Edition in English*, vol. 39, p. 3055-3059 (2000).

Niemeyer, C. M., et al., "Covalent DNA-Streptavidin conjugates as building blocks for novel biometallic nanostructures," *Angewandte Chemie International Edition in English*, vol. 37, p. 2265-2268 (1998).

Posner, G. H., et al., "A Mechanistic and synthetic study of organocopper substitution reactions with some homoallytic and cyclopropylcarbinyl substrates application to isoprenoid synthesis," *Tetrahedron*, vol. 32, p. 2281-2287 (1976).

Schwab, P., et al., "A series of well-defined metathesis catalysts synthesis of $RuCi_2(=CHR')(PR3)2$ 1 and its reactions," *Angewandte Chemie International Edition in English*, vol. 34, p. 2039-2041 (1995).

Shchepinov, M. S., et al., "Oligonucleotide dendrimers: stable nano-structures," *Nucleic Acids Research*, vol. 27, p. 3035-3041 (1999).

Storhoff, J. J., et al., "One-pot colorimetric differentiation of polynucleotides with single base imperfections using gold nanoparticle probles," *Journal of the American Chemical Society*, vol. 120, p. 1959-1964 (1998).

Storhoff, J. J., et al., "Programmed Materials Synthesis with DNA," *Chemical Reviews*, vol. 99, p. 1849-1862 (1999).

Taton, T. A., et al., "Scanometric DNA array detection with nanoparticle probes," *Science*, vol. 289, p. 1757-1760 (2000).

Trnka, T. M., et al., "The development of $L2X2Ru=CHR$ olefin metathesis catalysts: an organometallic success story," *Accounts of Chemical Research*, vol. 4, p. 18-29 (2001).

Watson, K. J., et al., "DNA-Block copolymer conjugates," *Journal of the American Chemical Society*, vol. 123, p. 5592-5593 (2001).

Watson, K. J., et al., "Hybrid Nanoparticles with block copolymer shell structures", *Journal of the American Chemical Society*, vol. 121, p. 462-463 (1999).

Yu, C. J., et al., "Electronic detection of single-base mismatches in DNA with ferrocene-modified probes," *Journal of the American Chemical Society*, vol. 123, p. 11155-11161 (2001).

Breslow, S.D., "Metathesis Polymerization," in *Progress in Polymer Science*, vol. 18, p. 1141-1195, (1993).

Grubbs, R., et al., "Polymer Synthesis and Organotransition Metal Chemistry," in *Science*, vol. 243, p. 907-915.

Ivin, K.J., et al., "Monocyclic Alkenes and Polyenes," in *Olefin Methasis and Metathesis Polymerization*, Academic Press, San Diego, 2nd Edition, p. 260-339 (1997).

Ivin, K.J., et al., "Copolymers of Cycloalkenes," in *Olefin Methasis and Metathesis Polymerization*, Academic Press, San Diego, 2nd Edition, p. Chapter 14, p. 340-357 (1997).

Kiessling, L., "Bioactive Polymers," in *Alkene Metathesis in Organic Synthesis*, A. Füsther, Ed., Springer-Verlag: Berlin, p. 199-231 (1998).

Schrock, R.R., "Olefin Metathesis by Well-Defined Complexes of Molybdenum and Tungsten," in *Alkene Metathesis in Organic Synthesis*, A. Füsther Ed., Springer-Verlag: Berlin, p. 1-36 (1998).

Letsinger, R., et al., "Chemistry of Oligonucleotide-Gold Nanoparticle Conjugates," *Phosphorus, Sulfur and Silicon*, vol. 144, p. 359-362 (1999).

Letsinger, R., et al., "Use of a Steroid Cyclic Disulfide Anchor in Constructing Gold Nanoparticle—Oligonucleotide Conjugates," *Bioconjugate Chem*, p. 289-291 (2000).

Li Z., et al., "Multiple thiol-anchor capped DNA-gold nanoparticle conjugates," *Nucleic Acids Research*, vol. 30, p. 1558-1562 (2002).

Nuzzo R., et al., "Spontaneously Organized Molecular Assemblies. 3. Preparation and Properties of Solution Adsorbed Monolayers of Organic Disulfides on Gold Surfaces," *J. Am Chem. Soc.*, vol. 109, p. 2358-2368 (1987).

Otsuka, H., et al., "Quantitative and Reversible Lectin-Induced Association of Gold Nonoparticles Modified with □-Lactosyl-□-mercapto-poly(ethyleneglycol)," *J. Am Chem. Soc.*, vol. 123, p. 8226-8230 (2001).

Wuelfing, P., et al., "Nanometer Gold Clusters Protected by Surface-Bound Monolayers of Thiolated Poly(ethyleneglycol) Polymer Electrolyte," *J. Am Chem. Soc.*, vol. 120, p. 12696-12697 (1998).

Brada, et al., "Golden Blot"—Detection of Polyclonal and Monoclonal Antibodies Bound to Antigens on Nitrocellulose by Protein A-Gold Complexes, *Analytical Biochemistry*, vol. 42, pp. 79-83 (1984) U.S.

Dunn, et al., A Novel Method to Map Transcripts: Evidence for homology between an Adenovirus mRNA and Discrete Multiple Regions of the Viral Genome, *Cell*, vol. 12, pp. 23-36, (1997) U.S.

Hacker, High performance Nanogold—Silver in situ hybridisation, *Eur. J. Histochem*, vol. 42, pp. 111-120 (1998) U.S.

Ranki, et al., Sandwich hybridization as a covenient method for the detection of nucleic acids in crude samples, *Gene*, vol. 21, pp. 77-85 (1983) U.S.

Romano, et al., "An antiglobulin reagent labelled with colloidal gold for use in electron microscopy," *Immunochemistry*, vol. 11, pp. 521-522 (1974) Great Britain.

Mohanty J., et al. "Pulsed laser excitation of phosphate stabilized silver nanoparticles," *Proc. Indian Acd. Sci.*, vol. 112, No. 1, p. 63-72.

Nicewarner-Peña S., et al., "Hybridization and Enzymatic Extension of Au Nanoparticle-Bound Oligonucleotides," *J. Am. Chem. Soc.*, vol. 124, p. 7314-7323 (2002).

Whitesides G.M., et al., "Soft Lithography in Biology and Biochemistry," *Annu. Rev. Biomed. Eng.*, p. 335-373 (2001).

O.D. Velev, et al., "In Situ Assembly of Collordal Particles into Miniaturized Biosensors," *Langmuir*, vol. 15, No. 11, pp. 3693-3698, May 25, 1999.

Alivisators et al., "Organization of 'nanocrystal molecules' using DNA," *Nature*, vol. 382, pp. 609-611 (1996).

Bain, et al., "Modeling Organic Surfaces with Self-Assembled Monolayers," *Angew. Chem. Int. Ed. Engl.*, vol. 28, pp. 506-512 (1989).

Bradley, "The Chemistry of Transition Metal Colliods," *Clusters and Colliods:From Theory to Applications*, G. Schmid, Editor, BCH, Weinheim, New York, pp. 459-542 (1994).

Brust et al., "Novel Gold-Dithiol Nano-Networks with Non-Metallic Electronic Properties," *Adv. Mater.*, vol. 7, pp. 795-797 (1995).

Chen et al., "A Specific Quadrilateral Synthesized from DNA Branched Junctions," *J. Am. Chem. Soc.*, vol. 111, p. 6402-6407 (1989).

Chen & Seeman, "Synthesis for DNA of a molecule with the connectivity of a cube," *Nature*, vol. 350, pp. 631-633 (1991).

Chen et al., Crystal Structure of a Four-Standed Intercalated DNA: d($C_4$)†‡*Biochem.*, vol. 33, pp. 13540-13546 (1994).

Dagani, "Supramolecular Assemblies DNA to organize gold nanoparticles," *Chemical & Engineering News*, p. 6-7, Aug. 19, 1996.

Dubois & Nuzzo, "Synthesis, Structure, and Properties of Model Organic Surfaces," *Annu. Rev. Phys. Chem.*, vol. 43, pp. 437-464 (1992).

Elghanian et al., "Selective Colorimetric Detection of Polynucleotides Based on the Distance-Dependent Optical Properties of Gold Nanoparticles," *Science*, vol. 277, pp. 1078-1081 (1997).

Grabar et al., "Preparation and Characterization of Au Colloid Monolayers," *Anal. Chem.* vol. 67, pp. 735-743 (1995).

Hacia et al., "Detection of heterozygous mutations in BRCA1 using high density oligonucleotide arrays and two-colour flourescence analysis," *Nature Genet.*, vol. 14, pp. 441-447 (1996).

Jacoby, "Nanoparticles change color on binding to nucleotide target," *Chemical & Engineering News*, p. 10, Aug. 25, 1997.

Letsinger et al., "Use of Hydrophobic Substituents in Controlling Self-Assembly of Oligonucleotides," *J. Am. Chem. Soc.*, vol. 115, pp. 7535-7536 (1993).

Letsinger et al., "Control of Excimer Emission and Photochemistry of Stilbene Units by Oligonucleotide Hybridization," *J. Am. Chem. Soc.*, vol. 116, pp. 811-812 (1994).

Marsh et al., "A new DNA nanostructure, the G-wire, imaged by scanning probe microscopy," *Nucleic Acids Res.*, vol. 23, pp. 696-700 (1995).

Mirkin, "H-DNA and Related Structures," *Annu. Review Biophys. Biomol. Struct.*, vol. 23, pp. 541-576 (1994).

Mirkin et al., "A DNA-based method for rationally assembling nanoparticles into macroscopic materials," *Nature*, vol. 382, pp. 607-609 (1996).

Mirkin et al., "DNA-Induced Assembly of Gold Nanoparticles: A Method for Rationally Organizing Colloidal Particles into Ordered Macroscopic Materials," *Abstract* 249, Abstracts of Papers Part 1, 212 ACS National Meeting 0-8412-3402-7, American Chemical Society, Orlando, FL, Aug. 25-29, 1996.

Mucic et al., "Synthesis and characterizations of DNA with ferrocenyl groups attached to their 5'-termini: electrochemical characterization of a redox-active nucleotide monolayer," *Chem. Commun.*, pp. 555-557 (1996).

Mulvaney, "Surface Plasmon Spectroscopy of Nanosized Metal Particles," *Langmuir*, vol. 12, pp. 788-800 (1996).

Rabke-Clemmer et al., "Analysis of Functionalized DNA Adsorption on Au(111) Using Electron Spectroscopy," *Langmuir*, vol. 10, pp. 1796-1800 (1994).

Roubi, "Molecular Machines—Nanodevice with rotating arms assembled from synthetic DNA," *Chemical &Engineering News*, p. 13, (Jan. 1999).

Seeman et al., "Synthetic DNA knots and catenanes," *New J. Chem.*, vol. 17, pp. 739-755 (1993).

Shaw & Wang, "Knotting of a DNA Chain During Ring Closure," *Science*, vol. 260, pp. 533-536 (1993).

Shekhtman et al., "Sterostructure of replicative DNA catenanes from eukaryotic cells," *New J. Chem.* vol. 17, pp. 757-763 (1993).

Smith and Feigon, "Quadruplex structure of Oxytricha telomeric DNA oligonucleotides," *Nature*, vol. 356, pp. 164-168 (1992).

Thein et al., "The use of synthetic oligonucleotides as specific hybridization probes in the diagnosis of genetic disorders," 2$^{nd}$ Ed., K.E. Davies, Ed., Oxford University Press, Oxford, New York, Tokyo, p. 21-33 (1993).

Wang et al., "Assembly and Characterization of Five-Arm and Six-Arm DNA Brached Junctions," *Biochem.*, vol. 30, pp. 5667-5674 (1991).

Wang et al., "A DNA Aptamer Which Binds to and Inhibits Thrombin Exhibits a New Structural Motif for DNA," *Biochem.*, vol. 32, pp. 1899-1904 (1993).

Weisbecker et al., "Molecular Self-Assembly of Aliphatic Thiols on Gold Colloids," *Langmuir*, vol. 12, pp. 3763-3772 (1996).

Wells, "Unusual DNA Structures," *J. Biol. Chem.*, vol. 263, pp. 1095-1098 (1988).

Zhang et al., "Informational Liposomes: Complexes Derived from Cholesteryl-conjugated Oligonucleotides and Liposomes," *Tetrahedron Lett.*, vol. 37, pp. 6243-6246 (1996).

Fraser. C., et al., "Synthesis of Glycopolymers of Controlled Molecular Weight by Ring-Opening Metathesis Polymerization Using Well-Defined Functional Group Tolerant Tutheniun Carbene Catalysts," *Macromolecules*, vol. 28, No. 21, p. 7248-7254 (1995).

Sinner, F., et al., "A New Class of Continous Polymer Supports Prepared by Ring-Opening Methatesis Polymerization: A straightfrorward Route to Functionalized Monoliths," *Macromolecules*, vol. 33, p. 5777-5786 (200).

Gittins, David L. et al., "Tailoring the Polyelectrolyte Coating of Metal Nanoparticles", *Journal of Physical Chemistry*, 105, pp. 6846-6852 (2001).

Fangcheng, Tang et al., Recent Advances in Olefin Metathesis Polymerization: Application to Synthesis of Block Copolymer and Functional Polymer, *Polymer Bulletin*, Ed., 3, pp. 144-153 (1997).

Kataby, G. et al., Coating of Amorphous Iron Nanoparticles by Long-Chain Alcohols, *Langmuir*, pp. 1512-1515 (1998).

\* cited by examiner

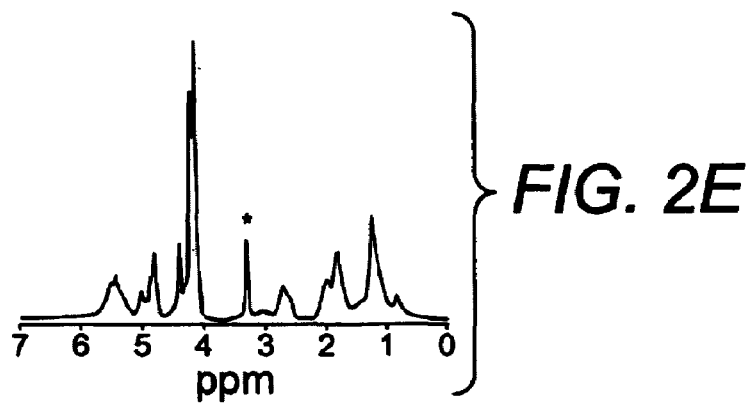

NANOPARTICLES WITH POLYMER SHELLS

This application claims benefit of provisional application 60/110,327 filed Nov. 30, 1998.

This invention was made with support from ARO through MURI, grant number DAAG55-97-1-0133. The U.S. government may have rights in the invention.

FIELD OF THE INVENTION

This invention relates to nanoparticles having polymer shells attached to them, the polymer shells imparting one or more selected properties to the nanoparticles. This invention also relates to a method of making the nanoparticles which utilizes a transition-metal, ring-opening metathesis polymerization of cyclic olefin derivatives, preferably norbornene derivatives, having a selected property. The method allows for the growth of the polymers off the surfaces of the nanoparticles. The invention also relates to certain novel monomers and polymers and to methods and kits for the detection or quantitation of an analyte.

BACKGROUND

In recent years, there has been considerable interest in developing methods for assembling nanoscale building blocks into periodic, functional materials. See Storhoff et al., *J. Clust. Sci.*, 8:179 (1997) and references cited therein, and Brousseau et al., *J. Am. Chem. Soc.*, 120:7645 (1998). These methods rely on access to both novel building block compositions and assembly strategies.

With regard to the former, both inorganic and organic compositions are now available. Importantly, some of these building blocks are accessible in macroscopic quantities and in monodisperse form. For example, a variety of methods exist for preparing monodisperse samples of CdS and CdSe particles (Murray et al., *J. Am. Chem. Soc.*, 115:8706 (1993); Weller, *Angew. Chem., Int. Ed. Engl.*, 32:41 (1993); Wang and Herron, *J. Phys. Chem.*, 95:525 (1991)) and gold particles (Grabar et al., *J. Anal Chem.*, 67:735 (1995); Frens, *Nature Phys. Sci.*, 241:20 (1973); Hayat, M. A. (ed.), *Colloidal Gold: Principles, Methods and Applications* (Academic, San Diego, 1991)) with diameters ranging from 1 to 40 nm. Studies involving these well-defined inorganic particles not only have led to a greater understanding of quantum confinement effects but also the development of new and useful spectroscopic methods (Freeman et al., *Science*, 267:1629 (1995); Zhu et al., *J. Am. Chem. Soc.*, 119:235 (1997)) and detection technologies (Mirkin et al., *Nature*, 382:607 (1996); Elghanian et al., *Science*, 277:1078 (1997); Storhoff et al., *J. Am. Chem. Soc.*, 120:1959 (1998)). Similarly, a great deal has been learned from the synthesis, characterization, and study of polymer particle compositions. Goodwin et al., *Colloid Polym. Sci.*, 525:464 (1974); Goodwin et al., *Colloid Polym. Sci.*, 257:61 (1979); Schmitt et al., *Adv. Mater.*, 9:61 (1997); José-Yacamán et al., *Appl. Phys. Lett.*, 7:913 (1969); Olsen and Kafafi, *J. Am. Chem. Soc.*, 113:7758 (1991); Spatz et al., *Adv. Mater.*, 8:337 (1996) However, far less is known about such systems with nanoscale dimensions (<100 nm).

The development of synthetic methods for preparing structures consisting of nanoparticle cores and organic polymer shells on this size scale would give entry into a new and versatile class of hybrid nanoparticle building blocks. Importantly, if it were possible to control the composition and thicknesses of the polymer shells, one would have unprecedented control over the chemical and physical properties of these novel materials.

SUMMARY OF THE INVENTION

The invention provides a method of preparing nanoparticles having at least one polymer shell attached thereto, each polymer shell having a selected property or properties. The method comprises attaching initiation monomers to the surfaces of the nanoparticles. Then, the nanoparticles having the initiation monomers attached to them are contacted with a transition metal, ring-opening, metathesis catalyst to activate the initiation monomers. The nanoparticles are also contacted with one or more types of propagation monomers of the formula P—L—N under conditions effective so that the monomers are polymerized to form one or more polymer shells attached to the nanoparticles. In the formula P—L—N, N is a cyclic olefin-containing group, P is a moiety which gives each polymer shell a selected property or properties, and L is a bond or linker. The invention also provides the nanoparticles, the initiation monomers, and propagation monomers wherein P is a moiety having a property selected from the group consisting of redox activity, optical activity, electronic activity and magnetic activity.

The invention further provides a method for detecting or quantitating an analyte comprising contacting a type of the nanoparticles of the invention with a sample suspected of containing the analyte and detecting or measuring the property or properties of the nanoparticles in order to detect or quantitate the analyte. The invention also provides a kit for detecting or quantitating an analyte comprising a container holding a type of the nanoparticles of the invention.

In addition, the invention provides a binding monomer. The binding monomer has the formula N—L—B, wherein B is a binding moiety that binds specifically to an analyte, and N and L are defined above.

The invention also provides a polymer formed by polymerizing one or more types of the propagation monomers of the invention. These polymers may be used to detect or quantitate an analyte when L comprises a binding moiety B. Thus, the invention also provides a method for detecting or quantitating an analyte comprising contacting a sample suspected of containing the analyte with the polymer and detecting or measuring the property or properties of the polymer in order to detect or quantitate the analyte. In addition, the invention provides a kit for detecting or quantitating an analyte comprising a container holding a polymer of the invention wherein L comprises a binding moiety B.

Finally, the invention provides a method of detecting or quantitating an analyte comprising contacting the analyte with a type of binding monomers of the invention so that the binding monomers bind to the analyte. Then, a type of propagation monomers of the invention is added so that the propagation monomers polymerize to form a polymer attached to the analyte. Then, the property(ies) of the polymer attached to the analyte is(are) detected or measured in order to detect or quantitate the analyte. Finally, the invention provides a kit for detecting or quantitating an analyte comprising a container holding a type of binding monomers of the invention, a container holding a type of propagation monomers of the invention, or both.

BRIEF DESCRIPTION OF THE DRAWINGS

FIGS. 2A–H: FIGS. 2A–E show the $^1$H NMR spectra of gold nanoparticles (GNPs) functionalized with a 3:1 mixture of 1-dodecanethiol and 2 (δ 7 to 0 ppm) (FIG. 2A), GNPs functionalized with a 3:1 mixture of 1-dodecanethiol and 2 (δ 6.3 to 5.2 ppm) (FIG. 2B), 2-modified GNPs after treatment with one equivalent of 1 (δ 6.3 to 5.2 ppm) (FIG. 2C), 2-modified GNPs after the addition of 20 equiv. of 3 to the ring-opening metathesis polymerization (ROMP) activated GNPs (δ 6.3 to 5.2 ppm) (FIG. 2D), and the GNP-poly 3-poly 4 hybrid system (δ 7 to 0 ppm) (FIG. 2E). FIGS. 2F–H show cyclic voltammetry of the GNP-poly 3 system (FIG. 2F), the GNP-poly 3-poly 4 hybrid (FIG. 2G), and poly 3 (FIG. 2H). All cyclic voltammetry experiments utilized a gold working electrode, a platinum-gauze counter electrode, and a silver-wire reference electrode. Ferrocene (bis(cyclopentadienyl)iron) was used as an internal reference.

Figure 1:
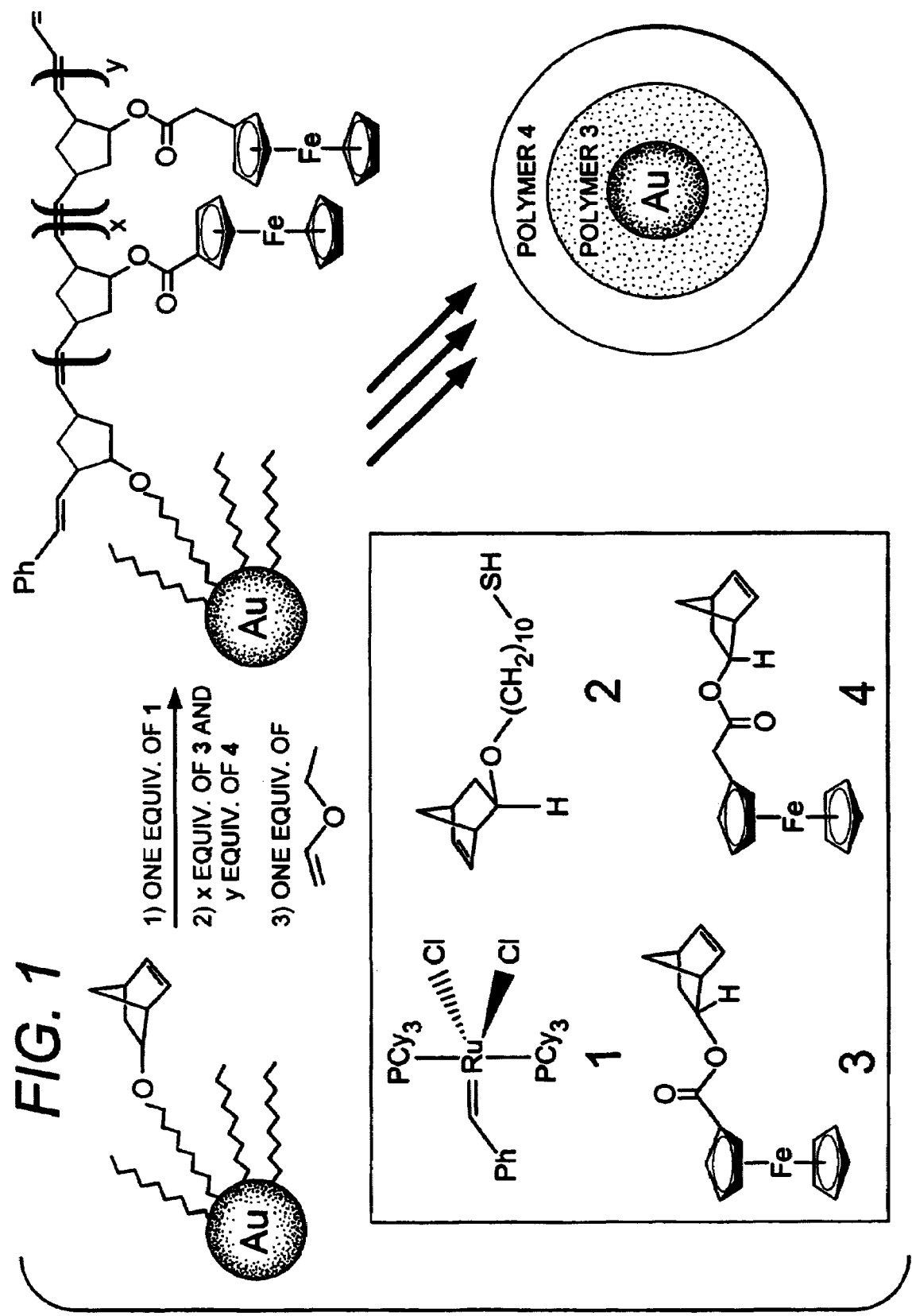
FIG. 1: Schematic diagram of the preparation of nanoparticles with block copolymer shells. Shown are the formulas of compounds 1, 2, 3 and 4. In the formula of 1, Ph=phenyl and Cy=cyclohexyl.

DETAILED DESCRIPTION OF THE
PRESENTLY PREFERRED EMBODIMENTS

Nanoparticles useful in the practice of the invention include metal (e.g. gold, silver, copper, and platinum), semiconductor (e.g., Si, CdSe, CdS, and CdS coated with ZnS), polymer (e.g., polystyrene and polymethylmethacrylate), magnetic (e.g., ferromagnetite), insulator (e.g., $SiO_2$), and superconductor (e.g., $YBa_2CU_3O_{7-8}$) colloidal materials. Other nanoparticles useful in the practice of the invention include ZnSe, ZnS, ZnO, $TiO_2$, AgI, AgBr, $HgI_2$, PbS, PbSe, PbTe, ZnTe, $SiO_2$, CdTe, $In_2S_3$, $In_2Se_3$, $In_2Te_3$, $Cd_3P_2$, $Cd_3As_2$, InAs, InP, GaP, and GaAs. Presently preferred are gold nanoparticles.

The size of the nanoparticles is preferably from about 1 nm to about 150 nm (mean diameter). More preferably the nanoparticles are from about 2 to about 100 nm. Most preferably the nanoparticles are from about 2 to about 30 nm.

Methods of making metal, semiconductor, and magnetic nanoparticles are well-known in the art. See, e.g., Schmid, G. (ed.) *Clusters and Colloids* (VCH, Weinheim, 1994); Hayat, M. A. (ed.) *Colloidal Gold: Principles, Methods, and Applications* (Academic Press, San Diego, 1991); Massart, R., *IEEE Transactions On Magnetics*, 17, 1247 (1981); Ahmadi, T. S. et al., *Science*, 272, 1924 (1996); Henglein, A. et al., *J. Phys. Chem.*, 99, 14129 (1995); Curtis, A. C., et al., *Angew. Chem., Int. Ed. Engl.*, 27, 1530 (1988); Brust et al., *J. Chem. Soc., Chem. Commun.*, 801 (1994); PCT application WO 98/21587.

Methods of making ZnS, ZnO, $TiO_2$, AgI, AgBr, $HgI_2$, PbS, PbSe, ZnTe, CdTe, $In_2S_3$, $In_2Se_3$, $Cd_3P_2$, $SiO_2$, $Cd_3As_2$, InAs, ZnSe, InP, GaP, and GaAs nanoparticles are also known in the art. See, e.g., Weller, *Angew. Chem., Int. Ed. Engl.*, 32, 41 (1993); Henglein, A., *Top. Curr. Chem.*, 143, 113 (1988); Henglein, *Chem. Rev.*, 89, 1861 (1989); Brus, *Appl. Phys. A.*, 53,465 (1991); Bahncmann, in *Photochemical Conversion and Storage of Solar Energy* (eds. Pelizetti and Schiavello 1991), page 251; Wang and Herron, *J. Phys. Chem.*, 95, 525 (1991); Olshavsky et al., *J. Am. Chem. Soc.*, 112, 9438 (1990); Ushida et al., *J. Phys. Chem.*, 95, 5382 (1992); PCT application WO 98/21587; Xu et al., *Mater. Res. Soc. Symp. Proc.*, 536, 401–405 (1999); Malik et al., *J. Mater. Chem.*, 8, 1885–1888 (1998); Haggata et al., *J. Mater. Chem.*, 7, 1969–1975 (1997); Pickett et al., *J. Mater. Chem.*, 7, 1855–1865 (1997); Micic et al., *J. Lumin.*, 70, 95–107 (1996); Micic et al., *J. Phys. Chem.*, 99, 7754–9 (1995); and Viano et al., *Nanostruct. Mater.*, 3, 239–44 (1993).

In addition, methods of making polymer nanoparticles are well known in the art. See, e.g., PCT application WO 98/21587; Gao, et al., *Chin. J. Polym. Sci.*, 17, 595–601 (1999); Okubo et al., *Colloid Polym. Sci.*, 277, 900–904 (1999); Cairns et al., *Langmuir*, 15, 8052–8058 (1999); Puig, *Rev. Mex. Fis.*, 45, 18–20 (1999); Chen et al., *J. Polym. Sci., Part A: Polym. Chem.*, 37, 2155–2166 (1999); Landfester et al., *Macromolecules*, 32, 5222–5228 (1999); Stork et al., *Polym. Mater. Sci. Eng.*, 80, 8–9 (1999); Xiangling et al., *Radiat. Phys. Chem.*, 54, 279–283 (1999); Charreyre et al., *J. Bioact. Compat. Polym.*, 14, 64–90 (1999); Sabel et al., PCT application WO 98/56361; Ming et al., *Macromolecules*, 32, 528–530 (1999); Schaertl et al., *Prog. Colloid Polym. Sci.*, 110, 285–290 (1998); Li et al., *Macromolecules*, 31, 6841–6844 (1998); Ming et al., *Macromol. Chem. Phys.*, 199, 1075–1079 (1998); Fritz et al., *J. Colloid Interface Sci.*, 195, 272–288 (1997); Zhang et al., *Macromolecules*, 30, 6388–6390 (1997); Cammas et al., *J. Controlled Release*, 48, 157–164 (1997); Larpent et al., *React. Funct. Polym.*, 33, 49–59 (1997); Huang et al., *Int. J. Polym. Mater.*, 35, 13–19 (1997); Holderle et al., *Polym. Prepr. (Am. Chem. Soc., Div. Polym. Chem.)*, 38, 479–480 (1997); Hoelderle, et al., *Book of Abstracts, 213th ACS National Meeting, San Francisco*, Apr. 13–17, 1997, OLY-206 (1997); Larpent et al., *Macromolecules*, 30, 354–362 (1997); Venier-Julienne et al., *Pharm. Acta Helv*, 71, 121–128 (1996); Levy et al., PCT applications WO 96/20698 and WO 99/53903; Banerjee et al., *Macromolecules*, 28, 3940–3 (1995); Maruyama et al., *Biomaterials*, 15, 103542 (1994); Stolnik et al., *J. Controlled Release*, 30, 57–67 (1994); Paulke et al., *Acta Polym.*, 43, 288–91 (1992); and Mueller, R. H.; Wallis, K. H. *Int. J. Pharm.*, 89, 25–31 (1993).

Finally, methods of making superconductor nanoparticles are also well known in the art. See, e.g., Geohegan et al., *Appl. Phys. Lett.*, 74, 3788–3790 (1999); Fukunaga et al., *Mater. Trans., JIM*, 40, 118–122(1999); Awano et al., *World Congr. Part. Technol*, 3, 1692–1699 (1998); Fukunaga et al., *J. Mater. Res.*, 13, 2465–2471 (1998); Terrones et al., *Appl. Phys. A: Mater. Sci. Process.*, A66, 307–317 (1998); Reverchon et al., *Ind. Eng. Chem. Res.*, 37, 952–958 (1998); Chhabra et al., *Tenside, Surfactants, Deterg.*, 34, 156–158, 160–162, 164–168 (1997); Maser et al., *Adv. Mater. (Weinheim, Ger.)*, 9, 503–506 (1997); Fukunaga et al., *Proc.—Electrochem. Soc.*, 97-2, 24–35 (1997); Eastoe et al., *Curr. Opin. Colloid Interface Sci.*, 1, 800–805 (1996); Chhabra et al., *World Surfactants Congr., 4th*, 1, 67–99 (1996); Pillai et al., *Adv. Colloid Interface Sci.*, 55, 241–69 (1995); Kumar et al., *Mater. Lett.*, 16, 68–74 (1993); Kumar et al., *Appl. Phys. Lett.*, 62, 765–7 (1993); and Pillai et al, *Surfactant Sci. Ser.*, 66, 227–246 (1997).

Suitable nanoparticles are also commercially available from, e.g., Ted Pella, Inc. (gold), Amersham Corporation (gold) and Nanoprobes, Inc. (gold), BBI (gold), Bangs Laboratories (gold, polymers, silica, magnetic), Vector Laboratories (magnetic biopolymer), Polysciences (silica, polymers), Dynal, Inc. (polymer, magnetic), Accurate Polymers (polymer), Polymer Laboratories (polymer), PolyMicrospheres (polymer, magnetic), Sphereotech (polymer, fluorescent, magnetic), Xenopore (polymer), and Interfacial Dynamic Corp. (polymer).

Each nanoparticle will have a plurality of initiation monomers attached to it. An "initiation monomer" is a compound comprising a functional group, which allows the initiation monomer to be attached to the nanoparticles, and a cyclic olefin group. The cyclic olefin group is located on the initiation monomer so that, when the initiation monomer is attached to the nanoparticles, the olefin functionality will be accessible to participate in the polymerization of subsequently-added cyclic olefin-containing propagation monomers (described below). This is accomplished by having the cyclic olefin group spaced apart from the functional group on the initiation monomer; preferably the cyclic olefin and the functional groups are at opposite ends of the initiation monomer. Thus, the immobilized initiation monomers, once activated by the addition of a suitable catalyst (described below), provide sites for the polymerization of the subsequently-added propagation monomers and allow for the selective growth of polymer blocks off the surfaces of the nanoparticles.

As used herein, "cyclic olefin" means a compound containing 1–3 rings, each ring containing 3 or more carbon atoms, preferably 5–8 carbon atoms, and the compound further containing at least one carbon—carbon double bond in a ring (the "olefin functionality"). The cyclic olefin must be capable of undergoing ring-opening metathesis polymerization (ROMP). Acyclic olefin is capable of undergoing ROMP when it contains sufficient strain in the ring(s) so that a ring-opening reaction will release the strain and provide the thermodynamic driving force for the formation of the polymer. For an estimate of ring strain, consult Greenberg & Liebman, *Strained Organic Molecules*, page 94 (Academic Press 1978). Preferably the cyclic olefin is norbornene, 7-oxonorbornene, cyclooctene, cyclooctadiene, cyclopentene, or cyclobutene. Most preferably, the cyclic olefin is norbornene.

Many compounds are known which can be attached to nanoparticles by means of a functional group (referred to hereinafter as "attachment compounds"). Methods of making these attachment compounds and attaching them to nanoparticles are well known. Preferably, the attachment compounds are stably attached to the surfaces of the nanoparticles by chemisorption of the molecules of the compound onto the nanoparticles or by covalent linkage of the molecules of the compound to the nanoparticles.

Suitable attachment compounds for use in the practice of the invention, and the corresponding type(s) of nanoparticles to which they attach, include:

a. Compounds of the formula $R^1SH$, $R^1SSR^2$, $R^1SR^2$, $R^1NC$, $R^1CN$, $R^1CO_2H$, $R^1SO_2H$, $(R^1)_3P$, $(R^1)_3N$, or ArSH can be attached to gold nanoparticles;

b. Compounds of formula $R^1SH$, ArSH, or $(R^1)_3N$ can be attached to silver, copper, palladium, and semiconductor nanoparticles;

c. Compounds of the formula $R^1NC$, $R^2SH$, $R^1SSR^2$, or $R^1SR^2$ can be attached to platinum nanoparticles;

d. Compounds of the formula $R^1SH$ can be attached to GaAs and InP nanoparticles;

e. Organosilanes, including compounds of the formula $R_1SiCl_3$ and $R^1Si(OR^2)_3$, $(R^1COO)_2$, $R^1CH=CH_2$, $R^1Li$ and $R^1MgX$, can be attached to Si and $SiO_2$ nanoparticles;

f. Compounds of the formula $R^1COOH$ or $R^1CONHR^2$ can be attached to metal oxide nanoparticles;

g. Compounds of the formula $R^1SH$, $R^1NH_2$, $ArNH_2$, pyrrole, or pyrrole derivatives, wherein $R^1$ is attached to one of the carbons of the pyrrole ring, can be attached to cuprate high temperature superconductor nanoparticles;

h. Compounds of the formula $R^1COOH$ can be attached to aluminum, copper, silver, and platinum nanoparticles; and i. Compounds that are unsaturated, such as azoalkanes ($R^1NNR^3$) and isothiocyanates ($R^3NCS$), can be attached to silicon nanoparticles.

In the above formulas:

$R^1$ and $R^2$ each has the formula $X(CH2)_n$ and, if a compound is substituted with both $R^1$ and $R^2$, $R^1$ and $R^2$ may be the same or different;

$R^3$ has the formula $CH_3(CH_2)_n$;

n is 0–30;

Ar is an aryl; and

X is $-CH_3$, $-CHCH_3$, $-COOH$, $-CO_2(CH_2)_mCH_3$, $-OH$, $-CH_2OH$, ethylene glycol, hexa(ethylene glycol), $-O(CH_2)_mCH_3$, $-NH_2$, $-NH(CH_2)_mNH_2$, halogen, glucose, maltose, fullerene C60, a cyclic olefin, or a nucleic acid, where m is 0–30.

For a description of attachment compounds and their preparation and use, see Xia and Whitesides, *Angew. Chem. Int. Ed*, 37, 550–575 (1998) and references cited therein; Bishop et al., *Curr. Opinion Colloid & Interface Sci.*, 1, 127–136(1996); Calvert, *J. Vac. Sci. Technol. B*, 11, 2155–2163 (1993); Ulman, *Chem. Rev.*, 96:1533 (1996) (alkanethiols on gold); Dubois et al., *Annu. Rev. Phys. Chem.*, 43:437 (1992) (alkanethiols on gold); Ulman, *An Introduction to Ultrathin Organic Films: From Langmuir-Blodgett to Self-Assembly* (Academic, Boston, 1991) (alkanethiols on gold); Whitesides, *Proceedings of the Robert A. Welch Foundation 39th Conference On Chemical Research Nanophase Chemistry*, Houston, Tex. pages 109–121 (1995) (alkanethiols attached to gold); Mucic et al. *Chem. Commun.* 555–557(1996) (describes a method of attaching 3' thiol DNA to gold surfaces); U.S. Pat. No. 5,472,881 (binding of oligonucleotide-phosphorothiolates to gold surfaces); Burwell, *Chemical Technology*, 4, 370–377 (1974) and Matteucci and Caruthers, *J. Am. Chem. Soc.*, 103, 3185–3191 (1981) (binding of oligonucleotides-alkylsiloxanes to silica and glass surfaces); Grabar et al., *Anal. Chem.*, 67, 735–743 (binding of aminoalkylsiloxanes and for similar binding of mercaptoalkylsiloxanes); Nuzzo et al., *J. Am. Chem. Soc.*, 109, 2358 (1987) (disulfides on gold); Allara and Nuzzo, *Langmuir*, 1, 45 (1985) (carboxylic acids on aluminum); Allara and Tompkins, *J. Colloid Interface Sci.*, 49, 410–421 (1974) (carboxylic acids on copper); Iler, *The Chemistry Of Silica*, Chapter 6, (Wiley 1979) (carboxylic acids on silica); Timmons and Zisman, *J. Phys. Chem.*, 69, 984–990 (1965) (carboxylic acids on platinum); Soriaga and Hubbard, *J. Am. Chem. Soc.*, 104, 3937 (1982) (aromatic ring compounds on platinum); Hubbard, *Acc. Chem. Res.*, 13, 177 (1980) (sulfolanes, sulfoxides and other functionalized solvents on platinum); Hickman et al., *J. Am. Chem. Soc.*, 111, 7271 (1989) (isonitriles on platinum); Maoz and Sagiv, *Langmuir*, 3, 1045 (1987) (silanes on silica); Maoz and Sagiv, *Langmuir*, 3, 1034 (1987) (silanes on silica); Wasserman et al., *Langmuir*, 5, 1074 (1989) (silanes on silica); Eltekova and Eltekov, *Langmuir*, 3, 951 (1987) (aromatic carboxylic acids, aldehydes, alcohols and methoxy groups on titanium dioxide and silica); and Lec et al., *J. Phys. Chem.*, 92, 2597 (1988) (rigid phosphates on metals); Lo et al., *J. Am. Chem. Soc.*, 118, 11295–11296 (1996) (attachment of pyrroles to superconductors); Chen et al., *J. Am. Chem. Soc.*, 117, 6374–5 (1995) (attachment of amines and thiols to superconductors); Chen et al., *Langmuir*, 12, 2622–2624 (1996) (attachment of thiols to superconductors); McDevitt et al., U.S. Pat. No. 5,846,909 (attachment of amines and thiols to superconductors); Xu et al., *Langmuir*, 14, 6505–6511 (1998) (attachment of amines to superconductors); Mirkin et al., *Adv. Mater.* (Weinheim, Ger.), 9, 167–173 (1997) (attachment of amines to superconductors); Hovis et al., *J. Phys. Chem. B*, 102, 6873–6879 (1998) (attachment of olefins and dienes to silicon); Hovis et al., *Surf. Sci.*, 402–404, 1–7 (1998) (attachment of olefins and dienes to silicon); Hovis et al., *J. Phys. Chem. B*, 101, 9581–9585 (1997) (attachment of olefins and dienes to silicon); Hamers et al., *J. Phys. Chem. B*, 101, 1489–1492 (1997) (attachment of olefins and dienes to silicon); Hamers et al., U.S. Pat. No. 5,908,692 (attachment of olefins and dienes to silicon); Ellison et al., *J. Phys. Chem. B*, 103, 6243–6251 (1999) (attachment of isothiocyanates to silicon); Ellison et al., *J. Phys. Chem. B*, 102, 8510–8518 (1998) (attachment of azoalkanes to silicon); Ohno et al., *Mol. Cryst. Liq. Cryst. Sci. Technol., Sect. A*, 295, 487–490 (1997) (attachment of thiols to GaAs); Reuter et al., *Mater. Res. Soc. Symp. Proc.*, 380, 119–24 (1995) (attachment of thiols to GaAs); Bain, *Adv. Mater.* (Weinheim, Fed Repub. Ger.), 4, 591–4 (1992) (attachment of thiols to GaAs); Sheen et al., *J. Am. Chem. Soc.*, 114, 1514–15 (1992) (attachment of thiols to GaAs); Nakagawa et al., *Jpn. J. Appl. Phys.*, Part 1, 30,3759–62 (1991) (attachment of thiols to GaAs); Lunt et al., *J. Appl. Phys.*, 70, 7449–67 (1991) (attachment of thiols to GaAs); Lunt et al., *J. Vac. Sci. Technol., B*, 9, 2333–6 (1991) (attachment of thiols to GaAs); Yamamoto et al., *Langmuir* ACS ASAP, web release number Ia990467r (attachment of thiols to InP); Gu et al., *J. Phys. Chem. B*, 102, 9015–9028 (1998) (attachment of thiols to InP); Menzel et al., *Adv. Mater.* (Weinheim, Ger.), 11, 131–134 (1999) (attachment of disulfides to gold); Yonezawa et al., *Chem. Mater.*, 11, 33–35 (1999) (attachment of disulfides to gold); Porter et al., *Langmuir*, 14, 7378–7386 (1998) (attachment of disulfides to gold); Son et al., *J. Phys. Chem.*, 98, 8488–93 (1994) (attachment of nitriles to gold and silver); Steiner et al., *Langmuir*, 8, 2771–7 (1992) (attachment of nitrites to gold and copper); Solomun et al., *J. Phys. Chem.*, 95, 10041–9 (1991) (attachment of nitriles to gold); Solomun et al., *Ber. Bunsen-Ges. Phys. Chem.*, 95, 95–8 (1991) (attachment of nitriles to gold); Henderson et al., *Inorg. Chim. Acta*, 242, 115–24 (1996) (attachment of isonitriles to gold); Huc et al., *J. Phys. Chem. B*, 103, 10489–10495(1999) (attachment of isonitriles to gold); Hickman et al., *Langmuir*, 8, 357–9 (1992) (attachment of isonitriles to platinum); Steiner et al., *Langmuir*, 8, 90–4 (1992) (attachment of amines and phospines to gold and attachment of amines to copper); Mayya et al., *J. Phys. Chem. B*, 101, 9790–9793 (1997) (attachment of amines to gold and silver); Chen et al., *Langmuir*, 15, 1075–1082(1999) (attachment of carboxylates to gold); Tao, *J. Am. Chem. Soc.*, 115, 4350–4358 (1993) (attachment of carboxylates to copper and silver); Laibinis et al., *J. Am. Chem. Soc.*, 114, 1990–5 (1992) (attachment of thiols to silver and copper); Laibinis et al., *Langmuir*, 7, 3167–73 (1991) (attachment of thiols to silver); Fenter et al., *Langmuir*, 7, 2013–16 (1991) (attachment of thiols to silver); Chang et al., *Am. Chem. Soc.*, 116, 6792–805 (1994) (attachment of thiols to silver); Li et al., *J. Phys. Chem.*, 98, 11751–5 (1994) (attachment of thiols to silver); Li et al., *Report*, 24 pp (1994) (attachment of thiols to silver); Tarlov et al., U.S. Pat. No. 5,942,397 (attachment of thiols to silver and copper); Waldeck, et al., PCT application WO/99/48682 (attachment of thiols to silver and copper); Gui et al., *Langmuir*, 7, 955–63 (1991) (attachment of thiols to silver); Walczak et al., *J. Am. Chem. Soc.*, 113, 2370–8 (1991) (attachment of thiols to silver); Sangiorgi et al., *Gazz. Chim. Ital.*, 111, 99–102 (1981) (attachment of amines to copper); Magallon et al., *Book of Abstracts*, 215th ACS National Meeting, Dallas, March 29–Apr. 2, 1998, COLL-048 (attachment of amines to copper); Patil et al., *Langmuir*, 14, 2707–2711 (1998) (attachment of amines to silver); Sastry et al., *J. Phys. Chem. B*, 101, 4954–4958 (1997) (attachment of amines to silver); Bansal et al., *J. Phys. Chem. B*, 102, 4058–4060 (1998) (attachment of alkyl lithium to silicon); Bansal et al., *J. Phys. Chem. B*, 102, 1067–1070 (1998) (attachment of alkyl lithium to silicon); Chidsey, *Book of Abstracts*, 214th ACS National Meeting, Las Vegas, NV September 7–11, 1997, I&EC-027 (attachment of alkyl lithium to silicon); Song, J. H., Thesis, University of California at San Diego (1998) (attachment of alkyl lithium to silicon dioxide); Meyer et al., *J. Am. Chem. Soc.*, 110, 4914–18 (1988) (attachment of amines to semiconductors); and Brazdil et al. *J. Phys. Chem.*, 85, 1005–14 (1981) (attachment of amines to semiconductors). Suitable initiation monomers for use in the practice of the invention include cyclic olefin-containing derivatives of these known attachment compounds having the formula:

wherein:

N is a cyclic olefin-containing group;

L is a bond or a linker whereby N is attached to A; and

A is an attachment compound-containing group.

The identity of A will depend on the identity of the material of which the nanoparticles are composed (see above).

In addition to being a bond, L can be a linker. As a linker, L can be any desired chemical group. For instance, L can be a polymer (e.g., polyethylene glycol, polymethylene, protein, peptide, oligonucleotide, or nucleic acid),

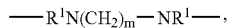

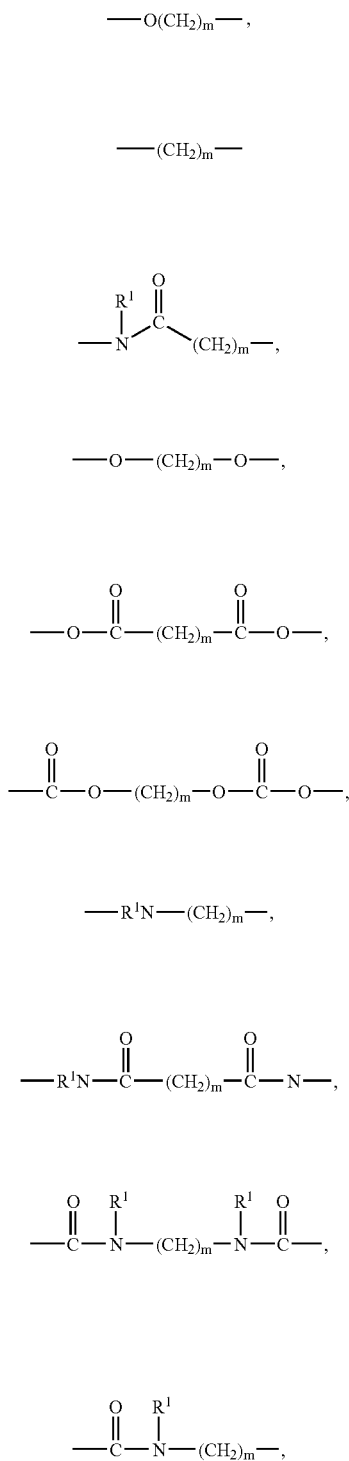

where $R^1$ is defined above and m is 0–30. L may also be or comprise a binding moiety B that binds specifically to an analyte (e.g., an antibody or oligonucleotide) (see below).

The initiation monomers can be synthesized by methods well known in the art. In particular, the synthesis of the initiation monomers utilizes standard organic chemistry synthetic procedures whereby the cyclic olefin-containing group, N, and the attachment compound-containing group, A, are coupled to each other through a bond or are sequentially coupled to the linker, L. See, e.g., Larock, *Comprehensive organic transformations: a guide to functional group preparations* (VCH Publishers, New York, N.Y., 1989) and *Comprehensive organic functional group transformations* (Katritzky et al., eds., Pergamon Press, New York, 1995).

Presently preferred as the initiation monomers for use on a variety of nanoparticles are norbornenyl-containing alkanethiols. Example 1 below describes a method which can be used for the preparation of such initiation monomers.

The initiation monomers can be attached to the nanoparticles in the same manner as the attachment compounds are attached to nanoparticles. Such methods are well known in the art. See, e.g., the references cited in the above discussion of attachment compounds. Generally, the nanoparticles and the initiation monomers are simply brought into contact and allowed to remain in contact for a sufficient time so that initiation monomers attach to the nanoparticles. Preferably a mixture of initiation monomers and corresponding attachment compounds (as diluent) are attached to the nanoparticles to reduce crosslinking of the initiation monomers and the propagating polymer during the subsequent polymerization. The ratio of initiation monomer to attachment compound that gives optimum results can be determined empirically and will depend on the type of initiation monomer, the type of attachment compound, and the type and size of the nanoparticles. By "corresponding attachment compound" is meant that the initiation monomers and attachment compounds are preferably, but not necessarily, of the same general type (e.g., alkanes) and preferably, but not necessarily, have the same functional group (e.g., thiol).

After the initiation monomers have been attached to the nanoparticles, the resulting nanoparticles are contacted with a catalyst to initiate the polymerization. The catalyst is a transition metal ring-opening metathesis catalyst. Many such catalysts suitable for use with cyclic olefin derivatives are known. See, e.g., U.S. Pat. Nos. 4,250,063, 4,727,215, 4,883,851, 4,945,135, 4,945,141, 4,945,144, 5,146,033, 5,198,511, 5,266,665, 5,296,566, 5,312,940, 5,342,909, 5,728,785, 5,750,815, 5,831,108, 5,849,851, and references cited therein; Schwab et al., *Angew. Chem. Int. Ed. Engl.*, 34:2039 (1995); Lynn et al., *J. Am. Chem. Soc.*, 120:1627 (1998).

Preferred are a family of function-group tolerant catalysts having the following formula:

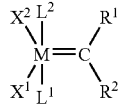

wherein: M may be osmium (Os) or ruthenium (Ru); $R^1$ is hydrogen; $X^1$ and $X^2$ may be different or the same and are any anionic ligand; $L^1$ and $L^2$ may be different or the same and are any neutral electron donor; and $R^2$ may be hydrogen, substituted or unsubstituted alkyl, or substituted or unsubstituted aryl. $X^1$ and $X^2$ are most preferably the same and are —Cl. $L^1$ and $L^2$ are preferably phosphines of the formula $PhosR^3R^4R^5$, where Phos is phosphine, $R^3$ is a secondary alkyl or cycloalkyl, and $R^4$ and $R^5$ (which may be the same or different) are aryl, $C_1$–$C_{10}$ primary alkyl, secondary alkyl, or cycloalkyl. $L^1$ and $L^2$ are most preferably the same and are -Phos(cyclohexyl)$_3$, -Phos(cyclopentyl)$_3$, or Phos(isopropyl)₃. Preferably, R² is hydrogen, C₁–C₂₀ alkyl or aryl. The C₁–C₂₀ alkyl may optionally be substituted with one or more aryl, halide, hydroxy, C₁–C₂₀ alkoxy, or C₂–C₂₀ alkoxycarbonyl groups. The aryl may optionally be substituted with one or more C₁–C₂₀ alkyl, aryl, hydroxyl, C₁–C₅ alkoxy, amino, nitro, or halide groups. The most preferred catalyst is compound 1 shown in FIG. 1. The preparation of these catalysts and conditions for their use are described in Schwab et al., *Angew. Chem. Int. Ed. Engl.*, 34:2039 (1995), Lynn et al., *J. Am. Chem. Soc.*, 120:1627 (1998), and U.S. Pat. No. 5,831,108, the complete disclosures of which are incorporated herein by reference. These catalysts produce a living polymerization having numerous attributes, including exceptional control over polymer length and chemical composition, and particle size, solubility, and shape.

Also preferred is a family of catalysts comprising a rhenium (VII) atom centrally linked to an alkylidene ligand (CR¹), an alkylidyne ligand (CHR²), and two other ligands (R³ and R⁴), at least one of which is an electron withdrawing ligand which is sufficiently electron withdrawing to render the rhenium atom electrophilic enough for metathesis reactions. Thus, the catalysts have the formula Re(CR¹)(CHR²)(R³)(R⁴). R¹ is selected from the group consisting of an alkyl having 1–20 carbon atoms, an aryl having 6–20 carbon atoms, an araalkyl having 7–30 carbon atoms, halogen substituted derivatives of each, and silicon-containing analogs of each. R² is selected from the group consisting of R¹ or is a substituent resulting from the reaction of the Re=CHR² moiety of the catalyst with an olefin that is being metathesized. Examples of R¹ and R² include phenyl, t-butyl, trimethylsilyl, triphenyl, methyl, triphenylsilyl, tri-t-butyl, tri-t-butylsilyl, 2,6-diisopropylphenyl, 2,4,6-triisopropylphenyl, and 2,6-dimethylphenyl. R³ and R⁴ can be any group which is sufficiently electron withdrawing to render the rhenium atom electrophilic enough for metathesis reactions. While it is preferably that both R³ and R⁴ be electron withdrawing, the catalysts may contain only one electron withdrawing ligand. R³ and R⁴ can be individually selected from groups consisting of R¹, a halogen, triflate, and concatenated combinations of R³ and R⁴, wherein R³ and R⁴ individually may contain alkoxide oxygen atoms which are bound to the rhenium atom, provided that when R¹ and R² are t-butyl and R³ and R⁴ are the same, then R³ and R⁴ are groups other than t-butoxide, trimethylsiloxide, neopentyl or a halogen. Preferably R³ and R⁴ are both alkoxide ligands in which the alcohol corresponding to the electron withdrawing alkoxide ligands should have a pKa of about 9 or below. Suitable ligands which fall within this range include phenoxide, hexafluoro-t-butoxide and diisopropylphenoxide. Examples of concatenated R³ and R⁴ groups are pinacolate, 2,6-dimethyl-2,6-heptanediolate and propan-1,3-diolate. The catalysts are typically monomers. However, they can form dimers, oligomers or polymers if the R³ and R⁴ groups are small enough to permit bridging of two or more metal centers. These rhenium catalysts and their synthesis and use are described in U.S. Pat. No. 5,146,033, the complete disclosure of which is incorporated herein by reference.

An additional group of preferred catalysts are those having the formula: M(NR¹)(OR²)₂(CHR³). M is molybdenum or tungsten; R¹ and R² are alkyl, aryl, aralkyl, haloalkyl, haloaryl, haloaralkyl or a silicon-containing analog thereof; and R¹ is allyl, aryl, aralkyl or a substituent resulting from the reaction of the M=CHR³ moiety of said catalyst with an olefin being metathesized. The alkyls contain 1–20 carbon atoms, the aryls contain 6–20 carbon atoms, and the araalkyls contain 7–20 carbon atoms. Examples of R¹ include 2,6-diisopropylphenyl, 2,4,6-trimethylphenyl, 2,6-di-t-butylphenyl, pentafluorophenyl, tbutyl, trimethylsilyl, triphenylmethyl, triphenylsilyl, tri-t-butylsilyl, and perfluoro-2-methyl-2-pentyl. Examples of R² include t-butyl, trifluoro-t-butyl, perfluoro-t-butyl, perfluoro-2-methyl-2-pentyl, 2,6-diisopropylphenyl, pentafluorophenyl, trimethylsilyl, triphenylsilyl, tri-t-butylsilyl, and hexafluoro-t-butyl. R³ is initially t-butyl or phenyl but, since the M=CHR³ moiety of the catalyst is intimately involved in the catalytic reaction, the CHR³ ligand is replaced by another alkylidene fragment from the olefins that are being metathesized. This family of catalysts and their synthesis and use are described in U.S. Pat. No. 4,727,215, the complete disclosure of which is incorporated herein by reference.

The initiation monomers are activated with the catalyst by methods known in the art. See, e.g., those references cited above. Other suitable conditions and optimum conditions can be determined empirically.

After activation of the initiation monomers with the catalyst, a cyclic olefin-containing propagation monomer is added, and the propagation monomers are polymerized. The propagation monomers have the formula:

N—L—P wherein:
N is a cyclic olefin-containing group;
L is a bond or a linker whereby N is attached to P; and
P is any moiety which provides a selected property to the resulting polymer.

L is the same as described above for the initiation monomers.

P will impart a desired property to the resulting polymer and polymer-nanoparticle hybrids. Such properties include hydrophilicity, hydrophobicity, optical properties (e.g., fluorescence, color, or non-linear optical character), magnetic activity (e.g., unpaired electron), electronic activity (e.g., conducting polymer), selective ion binding (e.g., binding of Na⁺, Pb²⁺, etc.) using crown-ethers, and redox activity (e.g., ferrocene derivatives). Preferably, the property is an optical property or redox activity.

Many suitable cyclic olefin-containing propagation monomers are known. See, e.g., U.S. Pat. Nos. 4,250,063, 5,064,919, 5,117,327, 5,198,511, 5,200,470; Davies et al., *J. Chem. Soc. Perkin* 1, 433 (1973); Posner et al., *Tetrahedron*, 32, 2281 (1976). Other cyclic olefin-containing propagation monomers can be synthesized by standard organic chemistry synthetic procedures. In particular, the cyclic olefin moiety, N, and the moiety, P, are coupled to each other through a bond or are sequentially coupled to the linker, L, using well-known methods. See, e.g., Larock, *Comprehensive organic transformations: a guide to functional group preparations* (VCH Publishers, New York, N.Y., 1989) and *Comprehensive organic functional group transformations* (Katritzky et al., eds., Pergamon Press, New York, 1995). The synthesis of some propagation monomers is described in the Examples below.

Suitable conditions for polymerizing the propagation monomers include those known in the art for polymerizing cyclic olefin and cyclic olefin derivatives. See, e.g., U.S. Pat. Nos. 4,883,851, 4,945,135, 4,945,141, 4,945,144, 5,198, 511, 5,266,665, 5,296,437, 5,296,566, 5,312,940, 5,342,909, 5,728,785, 5,750,815, 5,831,108, 5,849,851, and references cited therein; Schwab et al., *Angew. Chem. Int. Ed. Engl.*, 34:2039 (1995); Lynn et al., *J. Am. Chem. Soc.*, 120:1627 (1998). Other suitable conditions and optimum conditions can be determined empirically.

In the polymerization, a single propagation monomer having a particular P group or a mixture of monomers having different P groups can be used to form a single polymer shell having a single or a plurality of properties. Also, polymerization of a single monomer or a mixture of monomers can be followed by polymerization of one or more additional monomers, together or singly, to form a plurality of polymer shells attached to the nanoparticles, each shell having a different property or properties.

The polymerization, and the resulting size(s) and properties of the polymer shell(s), can be controlled by suitable choices of the reaction conditions, including the catalyst, solvent, temperature, the type(s) of propagation monomer(s), the order of addition of the propagation monomer(s), and the amount(s) of the propagation monomer(s). Preferably, for greater control, the polymerization is halted by the addition of a compound that terminates polymerization. Suitable compounds are known in the art. See, e.g., those references cited above.

The polymer-nanoparticle hybrids of the invention have a variety of uses. For instance, they can be used as probes to detect or quantitate analytes. See, e.g., PCT application WO 98/04740; PCT application WO 98/21587; Storhoff et al., *J. Clust. Sci.,* 8:179 (1997); Brousseau et al., *J. Am. Chem. Soc.,* 120:7645 (1998); Freeman et al., *Science,* 267:1629 (1995); Zhu et al., *J. Am. Chem. Soc.,* 119:235 (1997); Mirkin et al., *Nature,* 382:607 (1996); Elghanian et al., Science, 277:1078 (1997); Storhoff et al., *J. Am. Chem. Soc.,* 120:1959 (1998).

Analytes that can be detected or quantitated according to the invention include polysaccharides, lipids, lipopolysaccharides, proteins, glycoproteins, lipoproteins, nucleoproteins, peptides, oligonucleotides, and nucleic acids. Specific analytes include antibodies, immunoglobulins, albumin, hemoglobin, coagulation factors, peptide and protein hormones (e.g., insulin, gonadotropin, somatotropin), non-peptide hormones, interleukins, interferons, other cytokines, peptides comprising a tumor-specific epitope (i.e., an epitope found only on a tumor-specific protein), cells (e.g., red blood cells), cell-surface molecules (e.g., CD antigens, integrins, cell receptors), microorganisms (viruses, bacteria, parasites, molds, and fungi), fragments, portions, components or products of microorganisms, small organic molecules (e.g., digoxin, heroin, cocaine, morphine, mescaline, lysergic acid, tetrahydrocannabinol, cannabinol, steroids, pentamidine, and biotin), etc. Nucleic acids and oligonucleotides that can be detected or quantitated include genes (e.g., a gene associated with a particular disease), viral RNA and DNA, bacterial DNA, fungal DNA, mammalian DNA (e.g., human DNA), cDNA, mRNA, RNA and DNA fragments, oligonucleotides, synthetic oligonucleotides, modified oligonucleotides, single-stranded and double-stranded nucleic acids, natural and synthetic nucleic acids, etc.

To serve as probes, the polymer-nanoparticle hybrids must have a binding moiety, B, attached to them that allows the polymer-nanoparticle hybrids to bind specifically to the analyte. Suitable binding moieties and methods of making them are well known in the art. For instance, essentially any analyte can be detected or quantitated using antibodies specific for the analyte. In addition, any molecule which binds specifically to the analyte can be used, and many such molecules are known in the art. For instance, nucleic acids can be detected or quantitated using oligonucleotides having a sequence which is complementary to at least a portion of the analyte nucleic acid. Also, lectins can be used to detect or quantitate polysaccharides and glycosylated proteins. As another example, a receptor can be used to detect its ligand and vice versa. Many other suitable binding moieties, B, are known.

The binding moiety B can be attached to the polymer-nanoparticle hybrids in a variety of ways. For instance, as noted above, the linker L of the initiation monomer or propagation monomer may be any desired chemical group. Thus, the linker L in the propagation monomer and/or the initiation monomer may comprise a binding moiety B, such as a protein (e.g., antibody), an oligonucleotide, etc., and the binding moiety will be incorporated into the polymer shell(s) attached to the nanoparticles. Preferably, when the S polymer-nanoparticle hybrids are used as probes, at least some of the propagation monomers have a linker L which comprises a desired binding moiety B. Alternatively, or in addition, a separate binding monomer may be attached to the polymer-nanoparticle hybrids after the polymerization of the propagation monomers has been completed. The binding monomers have the formula:

N—L—B, wherein:
N is a cyclic olefin-containing group;
L is a bond or a linker whereby N is attached to B; and
B is a binding moiety.
L is the same as described above for the initiation monomers and propagation monomers. Preferably, however, L does not comprise a binding moiety B.

The binding monomers are synthesized and attached to the polymer-nanoparticle hybrids in the same manner as the propagation monomers. The binding monomers or, preferably, a mixture of binding monomers and propagation monomers having a desired property or properties may be attached to the polymer-nanoparticle hybrids to form a final polymer shell on the nanoparticles. The ratio of binding monomers to propagation monomers in such a mixture is preferably as low as possible. In this manner, even a single instance of the binding of B to its analyte can lead to a large detectable signal.

To perform an assay according to the invention, a sample suspected of containing an analyte is contacted with a type of polymer-nanoparticle hybrids having binding moieties B attached thereto. Any type of sample can be used. For instance, the sample may be a biological fluid (e.g., serum, plasma, blood, saliva, and urine), cells, cell lysates, tissues, libraries of compounds (e.g., organic chemicals or peptides), solutions containing PCR components, etc. Conditions and formats for performing such assays are well known in the art (see, e.g., the references cited above) or can be determined empirically by those of ordinary skill in the art.

Finally, the property or properties of the polymer attached to the nanoparticles is (are) detected or measured in order to detect or quantitate the analyte. The properties are those described above. Preferably, the property is redox activity or optical activity (e.g., fluorescence or color). Methods of detecting and measuring these properties are well known in the art.

Figure 5A:
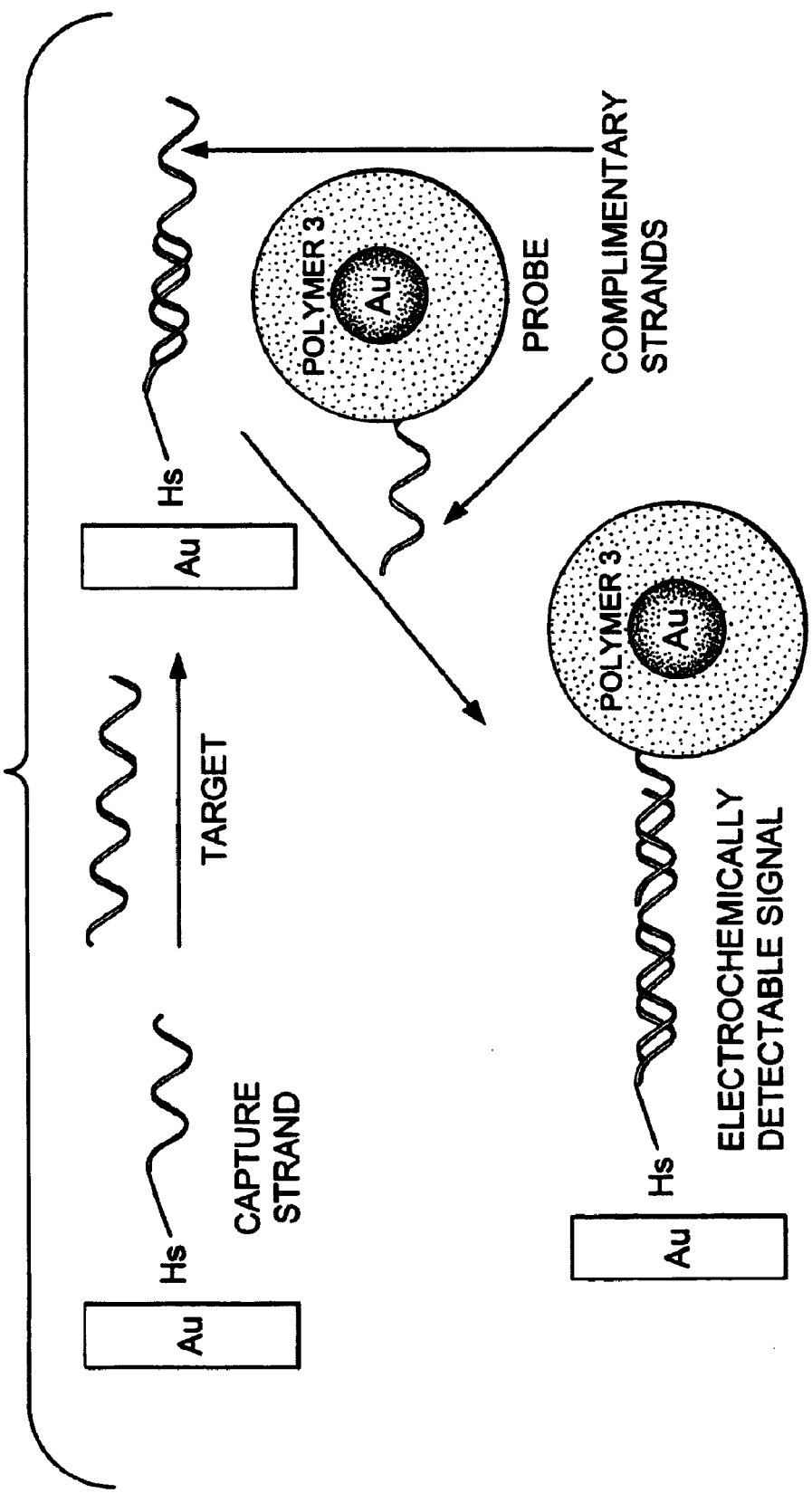
FIG. 5A: Diagram of an assay for the detection of nucleic acid (Target) using GNP-poly 3.

One format for detecting or quantitating nucleic acids is illustrated in FIG. 5A. As illustrated in FIG. 5A, capture oligonucleotides (Capture Strand) are attached to a gold substrate (e.g., a gold electrode). Methods of attaching oligonucleotides to gold and other substrates are known. See, e.g., those references cited above describing functional groups, particularly PCT application WO 98/0470. The capture oligonucleotides have a sequence complementary to at least a portion of the sequence of a nucleic acid analyte (Target), and the analyte nucleic acid is contacted with the substrate so that it binds to the capture oligonucleotides attached to the substrate. Then, polymer-nanoparticle hybrids having oligonucleotides attached to them are contacted with the analyte nucleic acid attached to the substrate. The oligonucleotides on the polymer-nanoparticle hybrids have a sequence complementary to at least a portion of the sequence of the analyte nucleic acid and bind to the analyte nucleic acid attached to the substrate. After removing unbound materials, the property of the polymer attached to the nanoparticles is detected or measured. As illustrated in FIG. 5A, the polymer is poly 3, a polymer which has redox activity, and this activity can be measured by cyclic voltammetry (see Example 1).

The invention further provides a kit for performing the assays for detecting or quantitating analytes. The kit comprises a container holding polymer-nanoparticle hybrids having binding moieties, B, attached to them. The kit may also contain other reagents and items useful for performing the assays. The reagents may include controls, standards, PCR reagents, hybridization reagents, buffers, etc. Other items which be provided as part of the kit include reaction devices (e.g., test tubes, microtiter plates, solid surfaces (possibly having a capture molecule attached thereto), syringes, pipettes, cuvettes, containers, etc.

The polymer-nanoparticle hybrids of the invention are also a new and versatile type of building block that chemists and material scientists can easily incorporate into many existing particle assembly strategies. See, e.g., PCT application WO 98/04740; Storhoff et al., *J. Clust. Sci.*, 8:179 (1997). For instance, after forming the desired polymer shell(s) on the nanoparticles, the polymers could be reacted with a small amount of either a termination monomer or a propagation monomer containing a functional group so that at least some of the polymers on the nanoparticles would be capped with functional groups that would allow the polymer-nanoparticle hybrids to be attached to other nanoparticles (made of the same or a different material) or to solid substrates made of metal, magnetic or semiconductor materials (see above description of the materials from which the nanoparticles are made). "Termination monomers" are the same as the initiation monomers described above, and the "functional groups" referred to in this paragraph are the same ones referred to in the discussion of initiation monomers.

The novel cyclic olefin-containing monomers of the invention can also be polymerized alone (i.e., not attached to nanoparticles) in the same manner as described above. Such polymers can be used in a variety of ways. For instance, polymers composed of propagation monomers wherein L comprises a binding moiety B (e.g., an oligonucleotide) can be used to detect and/or quantitate analytes by detection of the property or properties of the P groups.

The invention further provides a kit for performing the assays for detecting or quantitating analytes. The kit comprises a container holding polymers formed from propagation monomers wherein L comprises a binding moiety B. The kit may also contain other reagents and items useful for performing the assays.

Figure 5B:
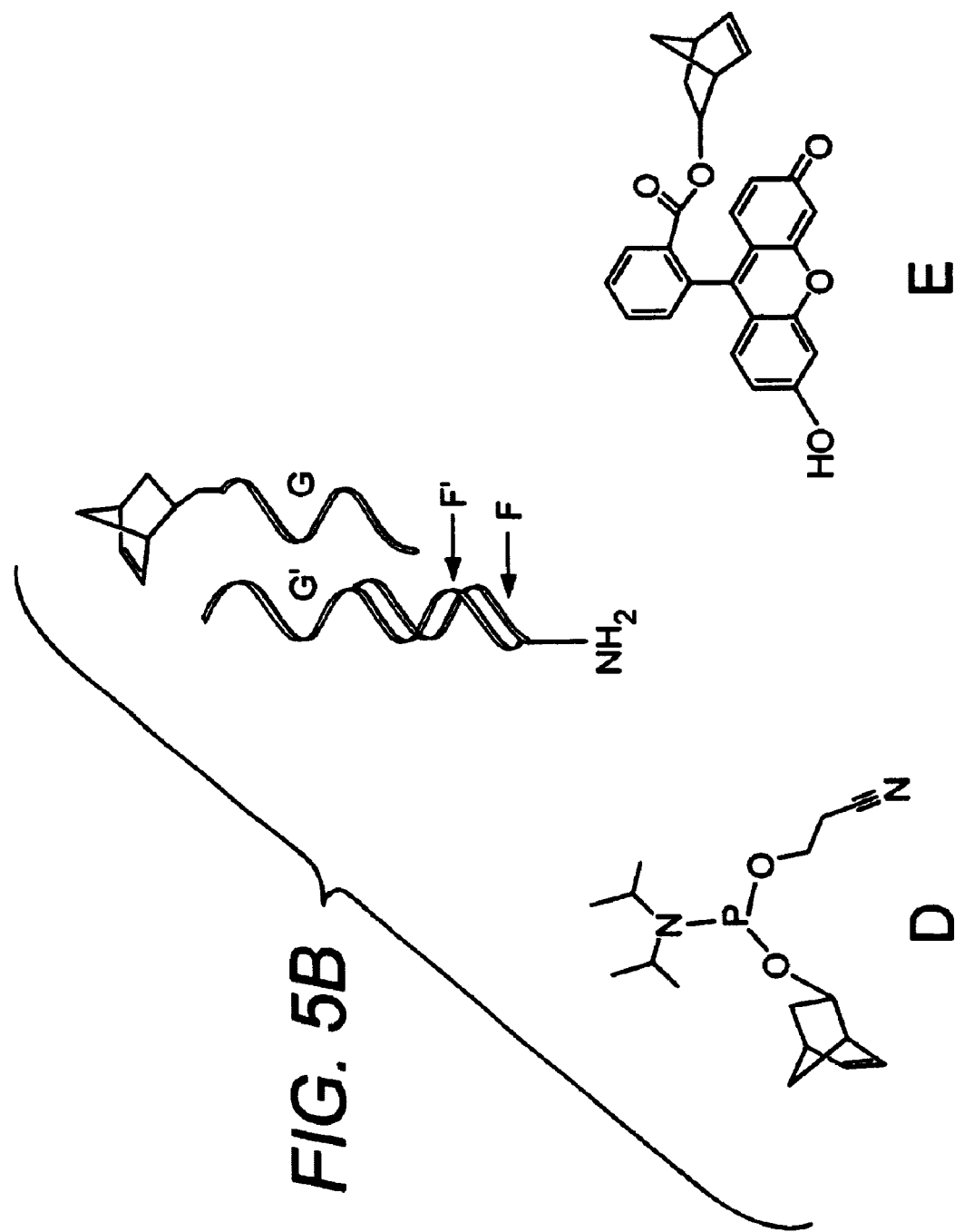
FIG. 5B: Diagram of an assay for the detection of nucleic acid using a fluorescent norbornenyl-containing monomer.

Further, propagation monomers wherein L comprises a binding moiety B can be used to detect and/or quantitate analytes by detection of the property or properties of the P groups. For instance, a format useful for the detection or quantitation of nucleic acids is illustrated in FIG. 5B. In this format, a single strand of DNA, F, is synthesized and modified at its 3' end to incorporate a functional group (e.g., an amino group) which is used for attachment of the DNA to a substrate (e.g., a transparent glass slide). See the discussion above of functional groups and their attachment to substrates. The sequence of F is complementary to at least a portion of the sequence of a target DNA, F'-H-G'. The G' sequence of the target DNA is complementary to a third DNA strand G which has been modified with a cyclic olefin-containing group (e.g., as illustrated, a norbornene group, prepared using the phosphoramidite D). After contacting the substrate having capture DNA F attached thereto with a sample suspected of containing the target DNA for a time sufficient to allow the target DNA to hybridize to F, the substrate is then contacted with G. After a time sufficient to allow G to hybridize to the target DNA, the substrate is then treated with a ROMP catalyst (e.g, catalyst 1, FIG. 1), followed by exposure to a cyclic olefin-containing fluorescent monomer (e.g. norbornene-modified fluorescein monomer E in hexanes) to produce fluorescent polymers attached to the DNA attached to the substrate. Since the cyclic olefin-modified DNA strand G is not complementary to the capturing strand F, exposing the substrate to the catalyst and then the fluorescent monomers will yield immobilized fluorescent polymer only if the target strand is present in the initial sample. Since a large excess of fluorescent monomer is used, the degree of polymerization on the substrate is dependent upon the reaction time, which is a tailorable quantity. The fluorescence can be readily detected using a fluorescence microscope. This strategy allows for the high sensitivity and flexibility for DNA detection and quantitation for a number of reasons. First, any target can be detected as long as the sequences of the ends of the strand (F' and G') are known. Second, by using two shorter DNA strands, F and G, complementary to the target, the DNA synthetic chemistry becomes easier and more quantitative than using a longer strand (e.g., F-G or F-H-G). Finally, since a single hybridization event can lead to the surface attachment of hundreds of fluorescent monomers, this technique can be ultra-sensitive (i.e., capable of detecting sub-femtomolar levels of DNA). Of course, other propagation monomers comprising different binding moieties and/or having different properties can also be used in this format for the detection of DNA and other analytes.

Finally, the invention provides a kit for performing the assays for detecting or quantitating analytes. The kit comprises a container holding propagation monomers wherein L comprises a binding moiety B. The kit may also contain other reagents and items useful for performing the assays.

As used herein, "a type of" refers to a plurality of the specified material having the same properties. For instance, "a type of" nanoparticles refers to nanoparticles which are the same (e.g., gold nanoparticles of a particular size). Similarly, "a type of" polymer-nanoparticle hybrids having binding moieties B attached to them refers to a plurality of nanoparticles having the same polymer(s) and binding moieties attached to them.

EXAMPLES

Example 1

This example describes the preparation of new metal-organic hybrid nanoparticles by the controlled growth of polymers from the surface of gold nanoparticle templates by ring-opening metathesis polymerization (ROMP) as illustrated in FIG. 1. In this methodology, a norbornenyl-termi nated linear alkanethiol (2) is used to modify the surfaces of organic-soluble gold nanoparticles (GNPs). Then, a functional group tolerant ROMP catalyst (1) is used to initiate polymerization directly from the particle surface, after which a norbornenyl-containing monomer feedstock is injected into the solution with the initiated nanoparticles.

Two proof-of-concept systems are presented. The first involves GNPs with a polymerized shell of a redox-active norbornenyl-functionalized ferrocene 3. The second involves GNPs functionalized with an initial block of 3 followed by a second block of another redox-active norbornenyl-containing monomer 4. The redox-potential of 4 is 220 mV more negative than that of 3, and the two can be easily differentiated by cyclic voltammetry. $^1$HNMR spectroscopy, cyclic voltammetry, and transmission electron microscopy (FIGS. 2A–H and FIGS. 3A–B) have been used to characterize the polymerization process and the resulting polymer-modified nanoparticles.

These studies indicate that the synthesis strategy can be used to prepare a new class of metal-organic hybrid nanoparticles that can be functionalized with polymeric layers of virtually any norbornenyl-containing or cyclic olefin-containing monomer. Since the process is a living polymerization, the attributes of this strategy are numerous, including exceptional control over polymer length and chemical composition, and particle size, solubility and shape.

A. Materials and General Methods

Unless otherwise noted, all reactions were carried out under a dry nitrogen atmosphere using standard Schlenk techniques or in an inert-atmosphere glovebox. Acetonitrile and dichloromethane were distilled over calcium hydride. Tetrahydrofuran (THF), benzene and diethyl ether were distilled over sodium/benzophenone. All solvents were distilled under nitrogen and saturated with nitrogen prior to use. Deuterated solvents were purchased from Cambridge Isotope Laboratories and used without further purification, except for CDCl$_3$, which was distilled over calcium hydride and vacuum transferred into an air-tight solvent bulb prior to transfer into the inert-atmosphere glovebox. Compounds 1, 2, 3, and 4 were synthesized as described below. All other reagents were purchased from Aldrich Chemical Company and used without further purification, unless otherwise noted. $^1$HNMR and $^{13}$CNMR spectra were recorded on a Varian Gemini 300 MHz FT-NMR spectrometer. For $^1$HNMR of samples containing gold nanoparticles, the line broadening was set at 1 Hz. GC-MS experiments were recorded on a Hewlett-Packard HP 6980 Series instrument equipped with an HP 5 column (the initial temperature was set at 50° C. for 2 minutes with a ramp of 20° C. per minute and a final temperature of 280° C.). Transmission electron microscopy (TEM) was performed on a Hitachi 8100 microscope. High resolution mass spectroscopy (HRMS) was performed on a VG 70-SE instrument. Elemental analysis was performed by Atlantic Microlab Inc. All flash column chromatography was performed using a 56 mm inner-diameter column using a 200 cm-long column of silica gel under a positive pressure of nitrogen, unless otherwise noted.

B. Synthesis of Catalyst 1

Catalyst 1 was synthesized using published procedures. Schwab et al., *Angew. Chem., Int. Ed. Engl.*, 34:2039 (1995); Lynn et al., *J. Am. Chem. Soc.*, 120:1627 (1998).

C. Synthesis of 1-mercapto-10-(exo-5-norbornen-2-oxy)-decane (2)

There are two key steps in the synthesis of metathesis-ready GNPs. The first involves the synthesis and characterization of 1-mercapto-10-(exo-5-norbornen-2-oxy)-decane, 2, which contains a ROMP-active norbornene segment attached to a long-chain alkanethiol. The exo-rather than the endo-isomer was chosen to optimize ROMP activity. Wolfe, P. S., Ph.D. dissertation, University of Florida (1997).

To prepare 2, exo-5-norbornen-2-ol (Posner et al., *Tetrahedron*, 32:2281 (1976); Davies et al., *J. Chem. Soc. Perkin 1*, 433 (1973); 1.00 g, 9.1 mmol) was weighed into a 50 mL Schlenk flask in an inert atmosphere glovebox. THF (15 ml) was added, and the solution was stirred vigorously while oil-free sodium metal (250 mg, 10.8 mmol) was added. The mixture was then taken out of the glovebox, refluxed for 12 hours under a positive stream of nitrogen, and allowed to cool to room temperature. In a separate 100 mL Schlenk flask, 10-chloro-decyl toluene-4 sulfonate (Tomohiro et al., *Synthesis*, 7:639 (1992)) (2.95 g, 9.5 mmol) was dissolved in THF (15 mL), and the flask was capped with a pressure-equalizing dropping funnel. The cooled solution of deprotonated exo-5-norbornen-2-ol was then transferred to the pressure-equalizing dropping funnel by cannula (excess Na was quenched with isopropanol) and slowly added to the decyl sulfonate ester solution with vigorous stirring over a period of 10 minutes. The dropping funnel was then replaced with a condenser, and the mixture was refluxed for an additional 12 hours under a positive stream of nitrogen. Upon cooling to room temperature, the reaction mixture was poured into ether (50 mL) and washed successively with water (50 mL), 0.1 M NaOH (50 mL), and brine (50 mL). The organic layer was collected, dried over sodium sulfate and filtered through a Buchner funnel. The solvent was removed on a rotary evaporator. Column chromatography of the slightly yellow oil on silica gel with 8% ether in hexanes as the eluent gave 1.94 g (6.9 mmol, 81%) of 1-chloro-10-(exo-5-norbornen-2-oxy)-decane as a clear oil. $^1$HNMR (CDCl$_3$): 1.05 (m, 20H), 3.56 (s, 1H), 3.72 (s, 1H), 3.95 (m, 5H), 5.80 (m, 1H), 6.31 (m, 1H). $^{13}$CNMR (CDCl$_3$): 26.33, 26.92, 28.92, 29.45, 29.49, 29.52, 30.12, 32.69, 34.48, 40.40, 45.26, 45.99, 46.44, 69.34, 80.22, 133.32, 140.61. GC-MS: One peak, retention time, 10.16 min; M$^+$: 284 m/z.

Potassium thioacetate (240 mg, 2.1 mmol) and the 1-chloro-10-(exo-5-norbornen-2-oxy)-decane (500 mg, 1.8 mmol) were weighed into separate 50 mL Schenk flasks in an inert atmosphere glovebox. The flasks were taken out of the glovebox, and degassed ethanol (10 mL) was transferred to each flask by cannula. The solution of 1-chloro-10-(exo-5-norborn-2-oxy)-decane was then transferred to the potassium thioacetate solution by cannula, and the mixture was refluxed for 20 hours under a positive stream of nitrogen. Upon cooling to room temperature, the mixture was poured into 120 (50 mL) and extracted with CH$_2$Cl$_2$ (3×50 mL). The combined organic extracts were washed with brine (3×50 mL), dried over sodium sulfate, and filtered through a Buchner funnel. The solvent was removed on a rotary evaporator. Column chromatography of the yellow oil on silica gel with CH$_2$Cl$_2$ as the eluent gave 488 mg of 1-(exo-5 norbornen-2-oxy)-10-(thioacetyl)-decane(1.5 mmol, 85%) as a clear oil. $^1$HNMR (CHCl$_3$): 1.35 (m, 15H), 1.58 (m, 4H), 1.72 (d, 1H), 2.83 (s, 1H), 2.9 (t, 3H), 3.48 (m, 3H), 5.93 (m, 1H), 6.20 (m, 1H). GC-MS: One peak, retention time, 11.34 min; M$^+$: 324 m/z.

Sodium methoxide (8.1 mg, 0.15 mmol) and the 1-(exo-5-norbornen-2-oxy)-10-(thioacetyl)-decane (488 mg, 1.5 mmol) were weighed into separate 50 mL Schenk flasks in an inert atmosphere glovebox. The two flasks were taken out of the glovebox, and degassed methanol (10 mL) was transferred to each flask by cannula. The solution of 1-(norborn-2-en-5-exo-ol)-10-(thioacetyl)-decane was then transferred by cannula to the sodium methoxide solution, and the mixture was refluxed for six hours under a positive stream of nitrogen. Upon cooling to room temperature, the mixture was poured into 1.0 M HCl (50 mL) and extracted with ether (3×50 mL). The combined organic extracts were washed with brine (3×50 mL), dried over sodium sulfate, and the solvent was removed on a rotary evaporator to give 361 mg of 1-mercapto-10-(exo-5-norbornen-2-oxy)-decane (1.23 mmol, 85%) of sufficient purity for further manipulations. $^1$HNMR ($C_6D_6$): 1.25 (m, 18H), 1.61 (q, 4H), 1.88 (d, 1H), 2.28 (q, 2H), 2.63 (s, 1H), 2.90 (s, 1H), 3.35 (m, 3H), 5.94 (m, 1H). GC-MS: One peak, retention time, 10.43 min; M$^+$: 282 m/z.

D. Synthesis of exo-5-norbornen-2-yl ferrocenecarboxylate (3)

Ferrocenecarboxylic acid (0.511 g, 2.22 mmol) was weighed into a 100 mL Schlenk flask. The flask was placed under nitrogen using standard Schlenk techniques. Dry dichloromethane (50 mL) was added by cannula, and oxalyl chloride (0.291 mL, 3.34 mmol) was syringed into the reaction vessel. The mixture was stirred at room temperature for 2 hours. The solvent and excess oxalyl chloride were removed by rotary evaporation, and dry benzene (50 mL) was added by cannula. Next, exo-5-norbornen-2-ol (0.244 g, 2.22 mmol) was weighed into a 250 mL round-bottom flask and placed under nitrogen using standard Schlenk techniques. Dry benzene (50 mL) was added by cannula, and triethylamine (0.62 mL, 4.44 mmol) was syringed into the reaction vessel. The acid chloride solution in the Schlenk flask was then transferred into the round-bottom flask containing the alcohol solution by cannula, and the mixture was refluxed under nitrogen for 12 hours. The solution was diluted with brine (100 mL) and extracted with benzene (3×100 mL). The benzene layers were combined, dried over magnesium sulfate, and the solvent was removed by rotary evaporation. Column chromatography on silica gel with pentane/ether (8:1) as the eluent gave 0.215 g (0.668 mmol, 30%) of desired product as a yellow solid. $^1$HNMR ($C_6D_6$): 1.58 (m, 4H), 2.59 (s, 1H), 2.98 (s, 1H), 4.02 (m, 7H), 4.85 (d, 2H), 4.97 (d, 1H), 5.79 (m, 1H), 5.98 (m, 1H). $^{13}$CNMR (CDCl$_3$): 34.78, 40.69, 46.37, 47.58, 69.69, 70.08, 71.19, 74.87, 132.85, 132.87, 141.15, 175.60. HRMS (EI) (M$^+$): calcd. for $C_{18}H_{18}O_2Fe$: 322.066 m/z; found: 322.066 m/z. Anal: calcd. for $C_{18}H_{18}O_2Fe$: C, 67.1; H, 5.63; Found: C, 66.9; H, 5.76.

E. Synthesis of exo-5-norbornen-2-yl ferroceneacetate (4)

Ferroceneacetic acid (0.401 g, 1.64 mmol) was weighed into a 100 mL Schlenk flask. The flask was placed under nitrogen using standard Schlenk techniques. Dry dichloromethane (50 mL) was added by cannula, and oxalyl chloride (0.232 mL, 2.66 mmol) was syringed into the reaction vessel. The mixture was stirred at room temperature for 2 hours. The solvent and excess oxalyl chloride were removed by rotary evaporation, and dry benzene (50 mL) was added by cannula. Next, exo-5-norbornen-2-ol (0.181 g, 1.64 mmol) was weighed into a 250 mL round-bottom flask and placed under nitrogen using standard Schlenk techniques. Dry benzene (50 mL) was added by cannula, and triethylamine (0.46 mL, 3.29 mmol) was syringed into the reaction vessel. The acid chloride solution in the Schlenk flask was then transferred into the round-bottom flask containing the alcohol solution by cannula, and the mixture was refluxed under nitrogen for 12 hours. The solution was diluted with brine (100 mL) and extracted with benzene (3×100 mL). The benzene layers were combined, dried over magnesium sulfate, and the solvent was removed by rotary evaporation. The benzene layers were passed through a short plug of silica gel (30 mm long, in a Pasteur pipette), and removal of the solvent on a rotary evaporator gave 0.281 g (0.84 mmol, 51%) of the desired product as a brown liquid. $^1$HNMR ($C_6D_6$): 1.58 (n, 4H), 2.59 (s, 1H), 2.90 (s, 1H), 3.19 (d, 2H), 3.95 (d, 2H), 4.02 (s, 5H), 4.19 (d, 2H), 4.80 (m, 1H), 5.75 (m, 1H), 5.98 (m, 1H). $^{13}$CNMR (CDCl$_3$): 34.45, 36.01, 40.35, 46.15, 47.36, 67.95, 68.46, 75.63, 80.95, 132.43, 141.50, 141.52, 171.55. HRMS (EI) (M$^+$): calcd. for $C_{19}H_{20}O_2Fe$: 336.081 m/Z; Found: 336.082 m/z.

F. Immobilization of 2 on GNPs and Characterization of the 2-Modified GNPs

The second key step in the preparation of metathesis-ready GNPs involves immobilization of 2 on 3 nm GNPs. The method of Schiffrin (Brust et al., *J. Chem. Soc., Chem. Commun.*, 801 (1994)) was modified for preparing 3 nm GNPs capped with linear alkanethiols by reducing HAuCl$_4$ (2.24 mmoles) in the presence of a 3:1 mixture of 1-dodecanethiol (1.68 mmoles), and 2 (0.56 mmoles) to yield GNPs modified with the two adsorbates. The dodecanethiol diluent molecule was employed to minimize surface crosslinking of norbornenyl groups and propagating polymer.

The GNPs can be precipitated from CH$_2$Cl$_2$ by the addition of ethanol and redispersed in various organic solvents such as hexanes, ether, and CH$_2$Cl$_2$. The $^1$HNMR spectrum of the modified particles in CDCl$_3$ confirms that the norbornene adsorbates are indeed attached to their surfaces, FIGS. 2A–B. The two resonances at approximately δ 5.9 and 6.2 are highly diagnostic of the two norbornenyl olefinic protons and compare well with those observed in the $^1$HNMR spectrum of 2 (δ 5.9 and 6.2) in CDCl$_3$. The UV-visible spectrum of these particles in hexanes exhibits a weak plasmon band at 518 nm, which is characteristic of gold nanoparticles of this size. Duff et al., *J. Chem. Soc. Chem. Commun.*, 96 (1993).

G. Synthesis and Characterization of GNP-poly 3

Inside an inert atmosphere glovebox, 3 nm GNPs modified with 2 (10 mg) were weighed into a screw-top NMR tube, and 100 μL of CDCl$_3$ was added. Catalyst 1 (1.5 mg, 1.8 μmol) was dissolved in 200 μL of CDCl$_3$ and syringed into the NMR tube containing the 2-modified GNPs. The NMR tube was capped and placed on a shaker for 10 minutes. Next, a solution of 3 (12 mg, 37 μmol in 200 μL of CDCl$_3$) was added, and the NMR tube was recapped and shaken for a further 30 minutes, after which time an $^1$HNMR spectrum was taken. The catalyst was quenched with ethyl vinyl ether (about 100 μL). Isolation of the particle-polymer hybrids (21 mg) was achieved by pouring the CDCl$_3$ solution into a vigorously stirring solution of hexanes (100 mL). The mother liquor was decanted, and the resulting dark brown precipitate was washed with hexanes (3×50 mL) and dried under vacuum. The precipitate was redispersable in numerous organic solvents, such as CH$_2$Cl$_2$ and THF.

Ring-opening metathesis of the norbornene rings on the GNPs with catalyst 1 (1 equivalent; the number of norbornenyl rings on the particles was estimated from elemental analysis and NMR titrations) was achieved in less than 10 minutes in $CDCl_3$. Evidence for this activation process is the loss of the olefinic resonances at δ 5.9 and 6.2, FIG. 2C.

Figure 2A:
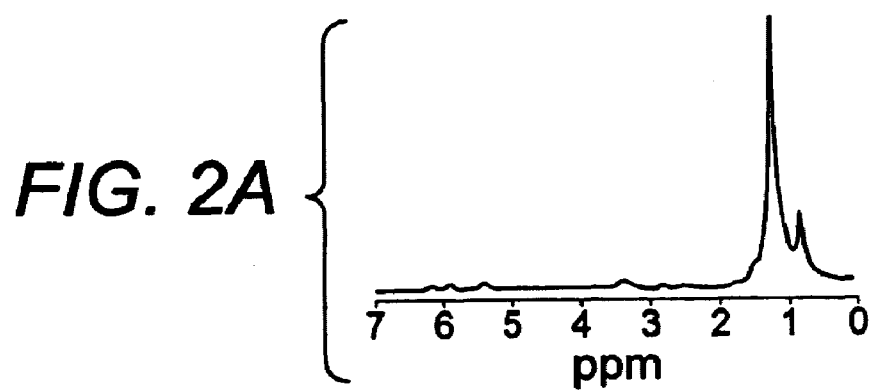
Figure 2B:
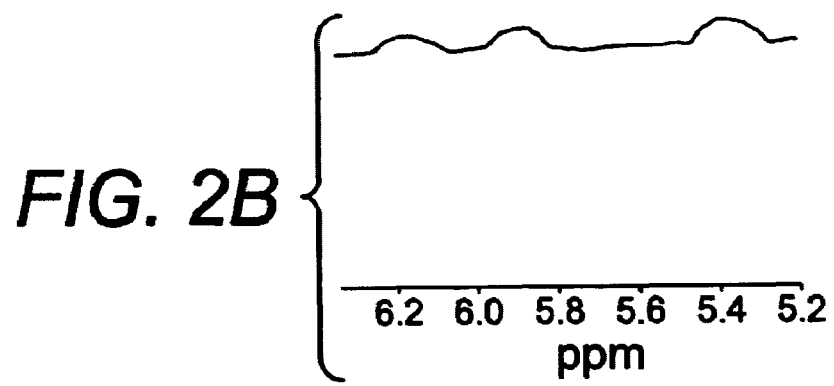
Figure 2C:
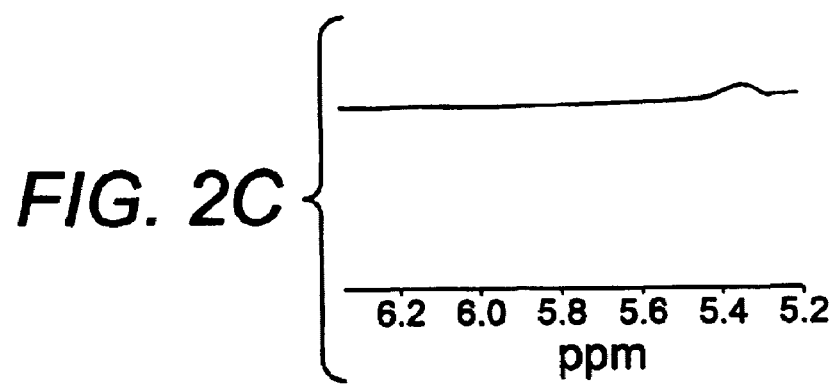
Figure 2D:
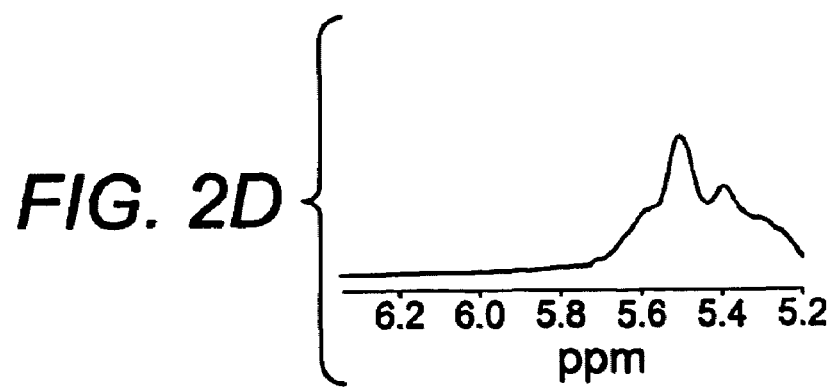

Subsequent addition of 20 equivalents of the redox-active complex 3 to this solution led to polymerization of 3, as evidenced by the appearance of broad resonances at δ 5.7–5.2 in the $^1$HNMR spectrum of the particle-polymer hybrids (GNP-poly 3), FIG. 2D. These resonances are characteristic of polymers synthesized from norbornenyl-containing starting materials. Schwab et al., *Angew. Chem., Int. Ed. Engl.*, 34:2039 (1995); Lynn et al., *J. Am. Chem. Soc.*, 120:1627 (1998). After 30 minutes there is no evidence of monomer 3, indicating that polymerization is complete.

The polymers could be terminated irreversibly by the addition of a slight excess of ethyl vinyl ether, a known ROMP termination agent for catalysts such as 1. Wu et al., *J. Am. Chem. Soc.*, 117:5503 (1995).

Significantly, the GNP-poly 3 hybrids could be precipitated from $CDCl_3$ with hexanes, a solvent in which the 2-modified GNPs were completely redispersable. Once washed thoroughly with hexanes, the GNP-poly 3 hybrids could be redispersed in a variety of more polar organic solvents, such as $CH_2Cl_2$ and THF. These solubility properties mirror those of the untethered ferrocenyl homopolymer, which was independently synthesized from 1 and 3 under nearly identical conditions (poly 3; see below).

Cyclic voltammetry of the GNP-poly 3 hybrids cast onto the surface of an Au/Si electrode in 0.1 M $TBAPF_6/CH_3CN$ ($TBAPF_6$=tetrabutyl ammonium hexafluorophosphate) exhibited a reversible wave associated with ferrocenyl oxidation/reduction at 180 mV versus $FcH/FcH^+$ (ferrocene/ferricinium), FIG. 2F.

Figure 3A:
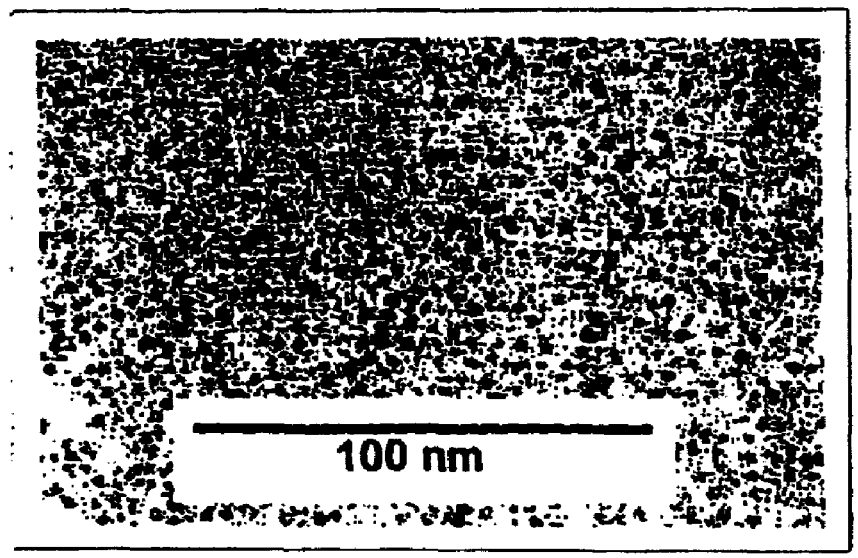
FIGS. 3A–B: Transmission electron microscopy (TEM) images of 2-functionalized GNPs (FIG. 3A) and GNP-poly 3 (FIG. 3B).
Figure 3B:
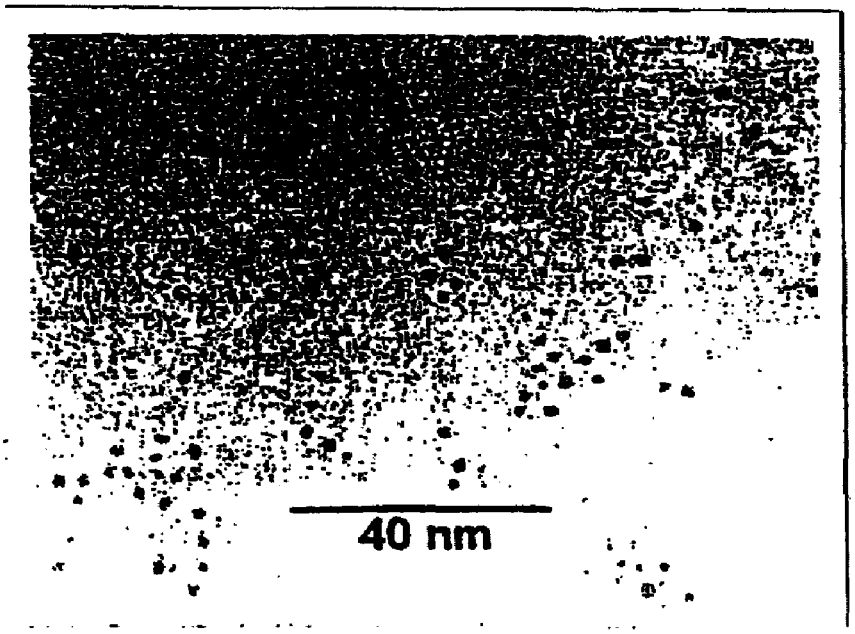

Finally, TEM analysis of the GNP-poly 3 hybrids indicated that the hybrid particles maintained their 3±1 nm diameter gold cores, but the polymer shell layers could not be imaged by TEM due to the low density of their atomic constituents, FIGS. 3A–B.

H. Synthesis and Characterization of GNP-poly 3-poly 4

As a further demonstration of the generality and scope of the strategy for preparing hybrid nanoparticles, block copolymers of two different norbornenyl ferrocenyl derivatives, 3 and 4, were grown successively from the surfaces of 2-modified particles treated with catalyst 1. Inside an inert atmosphere glovebox, 3 nm GNPs modified with 2 (10 mg) were weighed into a screw-top NMR tube, and 100 μL of $CDCl_3$ was added. Catalyst 1 (1 equivalent, 1.5 mg, 1.8 μmol) was dissolved in 200 μL of $CDCl_3$ and syringed into the NMR tube containing the 2-modified GNPs. The NMR tube was capped and placed on a shaker for 10 minutes. Next, a solution of 3 (20 equivalents, 12 mg, 37 μmol, in 200 μL of $CDCl_3$) was added, and the NMR tube was recapped and shaken for a further 20 minutes, after which time an $^1$HNMR spectrum was taken. Then, a solution of 4 (20 equivalents, 37 μmol, in 200 mL of $CDCl_3$) was added, and the NMR tube was recapped and shaken for another 20 minutes, after which time another $^1$HNMR spectrum was taken. The catalyst was quenched with ethyl vinyl ether (~100 μL). Isolation of the particle-polymer hybrids (32 mg) was achieved by pouring the $CDCl_3$ solution into a vigorously stirring solution of hexanes (100 mL). The mother liquor was decanted, and the resulting dark brown precipitate was washed with hexanes (3×50 mL) and dried under vacuum. The precipitate was redispersable in numerous organic solvents, such as $CH_2Cl_2$ and THF.

Compound 4 was chosen as the second polymer building block because it can be easily differentiated from 3 by cyclic voltammetry. The methylene group located between the carbonyl and ferrocenyl moiety in 4 makes it approximately 220 mV easier to oxidize than 3. Moreover, this methylene group provides a spectroscopic tag that allows allows one to follow the polymerization reaction by $^1$HNMR, FIG. 2E (note the asterisked resonance). The growth of the broad resonance at δ 3.3, coupled with the complete loss of resonances associated with the starting monomer 4, indicates complete conversion of 4 to a block of poly 4 (GNP-poly 3-poly 4).

The GNP-poly 3-poly 4 system exhibited reversible electrochemistry with the expected two distinguishable waves associated with oxidation/reduction of the two different types of ferrocenyl moieties within the particle immobilized block copolymer shell ($E_{1/2s}$=–40 mV for the block of poly 4 and 180 mV for the block of poly 3 vs $FcH/FCH^+$), FIG. 2G. A comparison of the integrated current associated with these two waves allows one to evaluate the relative amounts of 3 and 4 in the GNP-poly 3-poly 4 structure. Based on this analysis, a 1.4:1 ratio was calculated for 3 and 4 in the block copolymer. The reason that this is not a 1:1 ratio may be due to small differences in polymer solvation and, therefore, different degrees of electrochemical accessibility for the two layers or, alternatively, to stoichiometry errors due to the small amounts of reagents used. The ideal response associated with these waves (the peak current is linearly dependent upon the scan rate) and the lack of evidence for mediated electron transfer between the interior block of 3 and the electrode surface indicates that in these structures both polymer blocks are accessible to the electrode surface and solvated to the extent that ions can move in and out of the block copolymer structure. Significantly, both the homopolymers and the block copolymers formed from the polymerization of 3 and 4 exhibit broad waves characteristic of sluggish electron transfer and poor polymer solvation, FIG. 2H (poly 3 is given as an example).

Finally, TEM analysis of the GNP-poly 3-poly 4 hybrids indicated that the hybrid particles maintained their 3±1 nm diameter gold cores, but the polymer shell layers could not be imaged by TEM due to the low density of their atomic constituents.

I. Synthesis of Poly 3

A solution of 3 (12 mg, 37 μmol in 200 μL of $CDCl_3$) was syringed into a screw-top NMR tube, followed by the addition of a solution of 1 (1.5 mg, 1.8 μmol in 300 μL of $CDCl_3$). The NMR tube was capped and placed on a shaker for 30 minutes. The catalyst was quenched with ethyl vinyl ether (~100 μL). Isolation of the polymer (11 mg) was achieved by pouring the $CDCl_3$ solution into a vigorously stirring solution of hexanes (50 mL). The mother liquor was decanted, and the resulting light brown precipitate was washed with hexanes (3×25 mL) and dried under vacuum. The precipitate was redispersable in numerous organic solvents, such as $CH_2Cl_2$ and THF.

J. Control Experiment

As a control experiment, a solution consisting of the untethered ferrocenyl-containing poly 3 and 2-modified GNPs in a ratio comparable to that used for the GNP poly 3 experiment (see section G above) was prepared. When a precipitation experiment was carried out for this control system, the 2-modified GNPs remained soluble in hexanes (as evidenced by $^1$HNMR), while the homopolymer (poly 3) precipitated as expected. The difference in solubility between the 2-modified GNPs and the GNP-poly 3 hybrids is strong evidence that the polymers formed by surface polymerization are indeed tethered to the surfaces of the GNPs. Taken together, the data unambiguously confirm that the polymers grown off the surfaces of the GNPs remain attached to the particle surfaces.

These proof-of-concept results indicate that the particle synthesis strategy reported herein can be used to prepare a new class of nanoparticles that can be functionalized with polymeric layers of virtually any norbornenyl-containing monomer. Indeed, the strategy could be easily extended to other inorganic nanoparticle templates as well as optically active or electroactive norbornenyl groups. Traditional inorganic nanoparticles already have become the basis for many useful probe-type applications. Storhoff et al., *J. Clust. Sci.*, 8:179 (1997); Brousseau et al., *J. Am. Chem. Soc.*, 120:7645 (1998); Freeman et al., *Science*, 267:1629 (1995); Zhu et al., *J. Am. Chem. Soc.*, 119:235 (1997); Mirkin et al., *Nature*, 382:607 (1996); Elghanian et al., *Science*, 277:1078 (1997); Storhoff et al., *J. Am. Chem. Soc.*, 120:1959 (1998). The hybrid structures presented herein, with their high degree of synthetic tunability, are likely to become equally or even more important as diagnostic probes in chemical and biochemical detection strategies. Moreover, they are a new and versatile type of building block that chemists and material scientists can easily incorporate into many existing particle assembly strategies.

Example 2

Figure 4:
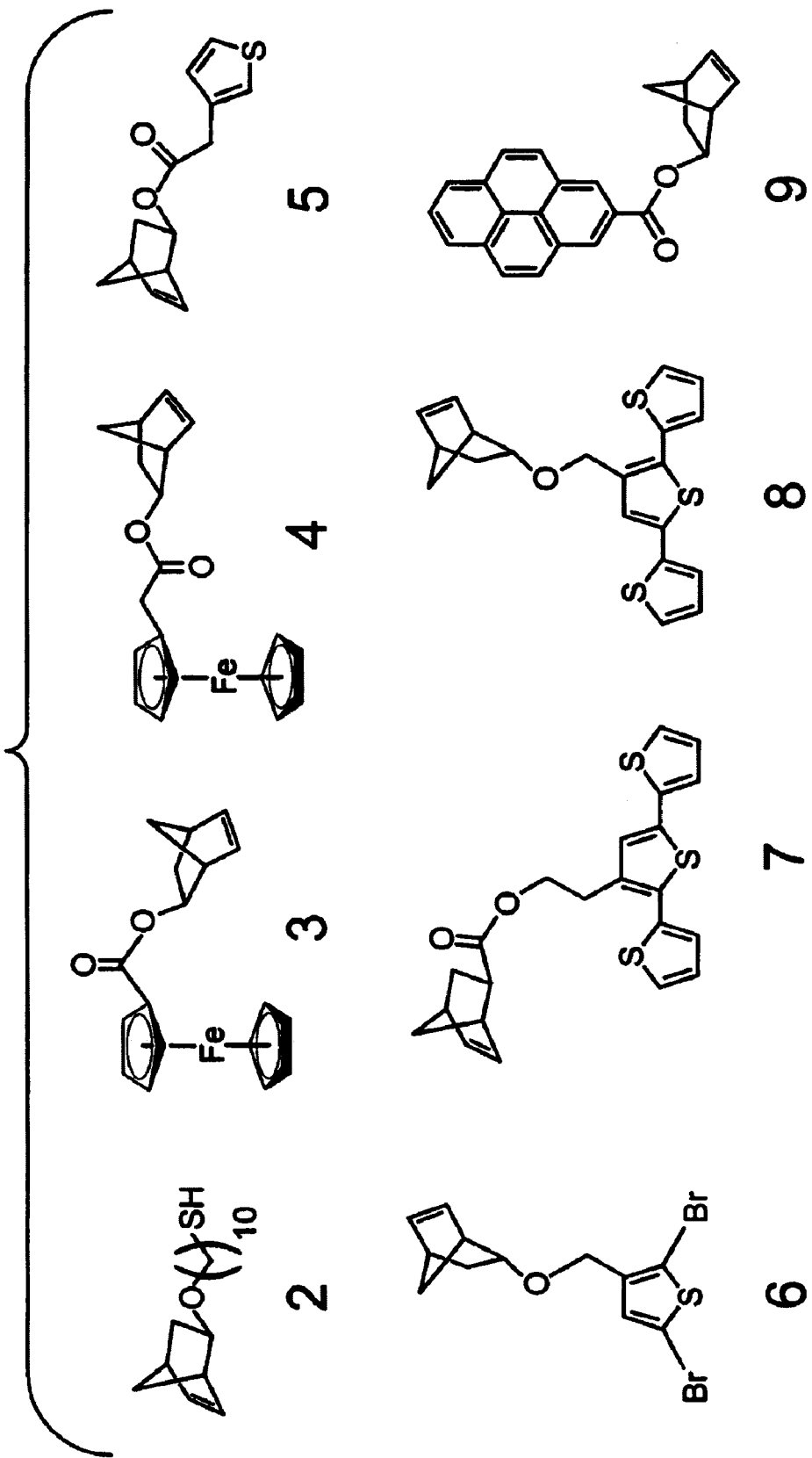
FIG. 4: Diagram showing the structures of norbornenyl-containing monomers.

This example describes the synthesis of compound 5 (see FIG. 4). To a 100 mL Schlenk flask 2-norbornene-5-exo-ol (1.10 g, 10 mmol), 3-thiopheneacetic acid (1.42 g, 10 mmol), and p-toluenesulfonic acid monohydrate (80 mg, 0.42 mmol) were added. The three solids were dissolved in toluene (60 mL) and a Dean/Stark trap was fitted to the top of the flask. A water condenser was placed on top of the Dean/Stark trap, and the mixture was heated to reflux. Over a period of six hours, the reaction volume was reduced to 20 mL by occasionally collecting solvent from the bottom of the Dean/Stark trap. The mixture was cooled to room temperature, poured into water (50 mL), and extracted with ether (3×50 mL). The organic portions were combined, washed with brine (50 mL), dried over sodium sulfate, and filtered into a 500 mL round bottom flask. The solvent was removed under vacuum using a rotary evaporator. The pale yellow oil was chromatographed on silica using a 1:1 mixture of $CH_2Cl_2$ and hexanes as an eluent to yield the desired product (1.68 g, 7.2 mmol, 72%) as a clear oil. $^1$H NMR ($CDCl_3$): 1.40 (m, 1H), 1.60 (m, 2H), 1.71 (m, 1H), 2.87 (b, 2H), 3.65 (s, 2H), 4.70 (d, 1H), 5.97 (m, 1H), 6.24 (m, 1H), 7.05 (d, 1H), 7.15 (b, 1H), 7.30 (m, 1H. $^{13}$C NMR ($CDCl_3$): 34.7, 36.3, 40.7, 46.3, 47.3, 75.8, 122.7, 125.7, 128.5, 132.6, 133.9, 141.2, 171.3. GCMS: Retention time 10.86 min, m/e$^+$ 234. Anal: cald. for $C_{13}H_{14}O_2S$: C, 66.64; H, 6.02; S, 13.68; Found: C, 66.91; H, 6.15; S, 13.86.

Example 3

This example describes the synthesis of compound 6 (see FIG. 4). In an inert atmosphere glovebox, exo-5-norbornen-2-ol (710 mg, 6.45 mmol) was weighed into a 50 mL Schlenk flask. THF (15 mL) was added, and the solution was stirred vigorously while oil-free sodium metal (160 mg, 6.96 mmol) was added. The mixture was then taken out of the glovebox, refluxed for 12 hours under a nitrogen bubble, and allowed to cool to room temperature. In a separate 100 mL Schlenk flask, 2,5-dibromo-3-bromomethyl-thiophene (2.01 g, 6.00 mmol) was dissolved in THF (15 mL), and the flask was capped with a pressure-equalizing dropping funnel. The cooled solution of deprotonated exo-5-norbornen-2-ol was then transferred to the pressure-equalizing dropping funnel by cannula (excess Na was quenched with isopropanol) and slowly added to the thiophene solution with vigorous stirring over a period of 10 minutes. The dropping funnel was then replaced with a condenser, and the mixture was refluxed for an additional 12 hours under a positive stream of nitrogen. Upon cooling to room temperature, the reaction mixture was poured into ether (50 mL) and washed successively with water (50 mL), 0.1 M NaOH (50 mL), 1 M HCl (50 ml), and brine (50 mL). The organic layer was collected, dried over sodium sulfate and filtered through a Buchner funnel. The solvent was removed on a rotary evaporator. Column chromatography of the slightly yellow oil on silica gel with 20% $CH_2Cl_2$ in hexanes as the eluent gave 1.88 g (5.16 mmol, 86%) of the desired product as a clear oil. $^1$H NMR ($CDCl_3$): 1.41 (m, 1H), 1.58 (m, 2H), 1.71 (m, 1H), 2.82 (b, 1H), 2.93 (b, 1H), 3.56 (m, 1H), 4.40 (m, 2H), 5.93 (m, 1H), 6.20 (m, 1H), 6.99 (m, 1H). $^{13}$C NMR ($CDCl_3$): 34.53, 40.47, 46.06, 65.12, 80.31, 109.59, 111.21, 131.03, 133.10, 139.80, 140.87. GCMS: Retention time 12.26 min, m/ζ 364.

Example 4

This example describes the preparation of compound 7 (see FIG. 4). In a 100 mL Schlenk flask was added 2-norbornene-5-exo-acetic acid (450 mg, 3.0 mmol). The flask was placed under nitrogen using standard Schlenk techniques. Dry $CH_2Cl_2$ (20 mL) was added by cannula, followed by oxalyl chloride (5 mL of a 2 M solution in $CH_2Cl_2$, 10 mmol). The mixture was allowed to stir for 2 hours at room temperature. The solvent and excess oxalyl chloride were removed under vacuum and the resulting acid chloride was redissolved in dry diethyl ether (20 mL). To a separate 100 mL Schlenk flask was added 3'-(2-hydroxyethyl)-2,2': 5',2"-terthiophene (850 mg, 2.91 mmol). The flask was placed under nitrogen, and diethyl ether (20 mL) was added followed by triethyl amine (0.84 mL, 6 mmol). The flask was fitted with a pressure equalizing dropping funnel. The norbornenyl-acid chloride solution was transferred to the dropping funnel by cannula and subsequently added to the stirring solution of the terthiophene solution dropwise over a period of ten minutes. The mixture was stirred for an additional 10 minures at room temperature and then poured into water (50 mL) and extracted with ether (3×50 mL). The organic portions were collected, washed with brine (50 mL), dried over sodium sulfate, and filtered into a 500 mL round bottom flask. The solvent was removed under vacuum using a rotary evaporator. The resulting oil was chromatographed on silica using 1:1 $CH_2Cl_2$ and pentane as an eluent to yield the desired product (1.15 g, 2.79 mmol, 96%) as alight green oil. $^1$HNMR ($CD_2Cl_2$): 1.32 (m, 2H), 1.45 (m, 1H), 1.86 (m, 1H), 2.87 (b, 1H), 2.98 (b, 1H), 3.10 (t, 2H), 4.32 (t, 2H), 6.11 (m, 2H), 7.05 (m, 1H), 7.10 (m, 2H), 7.19 (m, 2H), 7.26 (d, 1H), 7.37 (d, 1H). HRMS: calcd. for $C_{22}H_{20}O_2S_3$: 412.06; Found: 412.06.

Example 5

This example describes the preparation of compound 8 (see FIG. 4). $PdCl_2$ (1,1'-bis(diphenylphosphino)ferrocene)

(39 mg, 0.05 mmol) was weighed into a 100 ml Schlenk flask containing a magnetic stir bar and fitted with a reflux condenser and an addition funnel. The flask was evacuated to remove air, and a solution of 6 (1.00 g, 2.75 mmol) in dry diethyl ether (20 mL) was added by cannula. The flask was cooled to −20° C. in an acetone/ice bath, and a solution of (2-thienyl)magnesiumbromide (8.22 g, 1.54 mmol) in dry diethyl ether (20 mL) was added by addition funnel over a 30 min period. The reaction was allowed to warm to room temperature and was then refluxed overnight under a positive stream of nitrogen. The excess Grignard was consumed by the slow addition of a saturated solution of aqueous ammonium chloride to the organic layer, followed by three consecutive water washes (50 mL). The organic layer was collected, dried over sodium sulfate, and filtered into a 500 mL round bottom flask. The solvent was removed under vacuum using a rotary evaporator. The resulting dark brown oil was chromatographed on silica using 1:1 $CH_2Cl_2$ and hexanes as an eluent to yield the desired product (870 mg, 86%) as a green oil. $^1$HNMR ($CDCl_3$): 1.47 (m, 1H), 1.59 (m, 2H), 1.78 (m, 1H), 2.84 (b, 1H), 2.98 (b, 1H), 3.65 (m, 1H), 4.56 (m, 2H), 5.94 (m, 1H), 6.20 (m, 1H), 7.03 (m, 1H), 7.09 (m, 1H), 7.18 (m, 1H), 7.21 (m, 1H), 7.22 (m, 1H), 7.24 (m, 1H), 7.35 (m, 1H). $^{13}$C NMR ($CDCl_3$): GCMS: Retention time 18.73 min, m/e$^+$ 370.

Figure 7A:
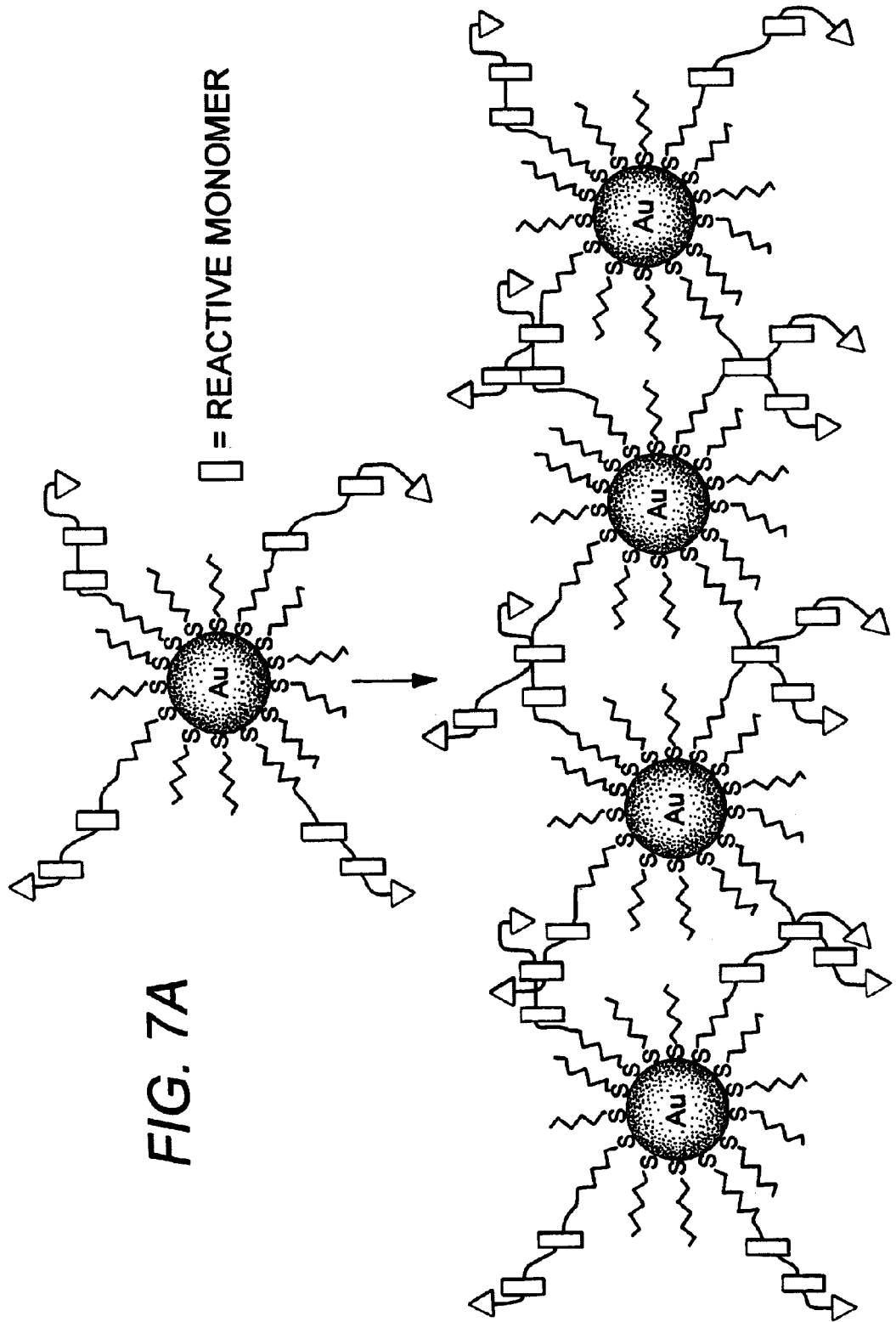
FIGS. 7A–B: Diagrams showing cross-linking of polymer-nanoparticle hybrids to produce nanoparticle polymer composites.
Figure 7B:
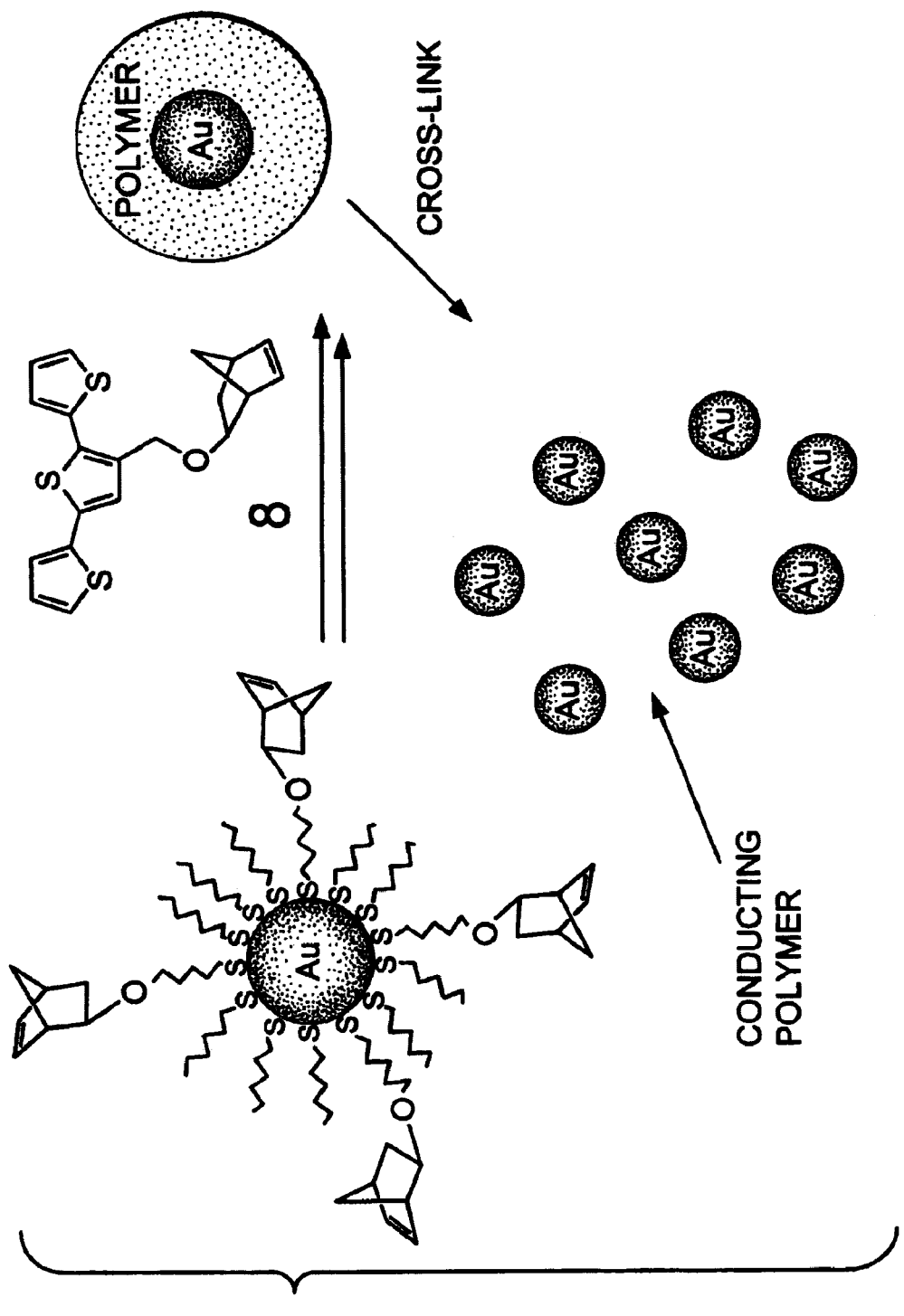

Monomers such as 5, 7, and 8 are doubly polymerizable monomers that can undergo ROMP chemistry followed by a second cross-linking reaction to give a conducting graft copolymer composite. With these new monomers, new nanoparticles/conducting polymer composites can be made (see FIGS. 7A–B).

Example 6

This example describes the synthesis of exo-5-norbornen-2-yl pyrenecarboxylate (compound 9 in FIG. 4). Pyrenecarboxylic acid (0.547 g, 2.22 mmol) was weighed into a 100 mL Schlenk flask. The flask was placed under nitrogen using standard Schlenk techniques. Dry dichloromethane (50 mL) was added by cannula, and oxalyl chloride (0.291 mL, 3.34 mmol) was syringed into the reaction vessel. The mixture was stirred at room temperature for 2 hours. The solvent and excess oxalyl chloride were removed by rotary evaporation, and dry benzene (50 mL) were added by cannula. Next, exo-5-norbornen-2-ol (0.244 g, 2.22 mmol) was weighed into a 250 mL round-bottom flask and placed under nitrogen using standard Schlenk techniques. Dry benzene (50 mL) was added by cannula, and triethylamine (0.62 mL, 4.44 mmol) was syringed into the reaction vessel. The acid chloride solution in the Schlenk flask was then transferred into the round-bottom flask containing the alcohol solution by cannula. The mixture was then refluxed under nitrogen for 12 hours. The solution was diluted with brine (100 mL) and extracted with benzene (3×100 mL). The benzene layers were combined, dried over magnesium sulfate, and the solvent was removed by rotary evaporation. Column chromatography on silica gel with pentane/ether (8:1) as the eluent gave 0.215 g (0.668 mmol, 30%) of the desired product as a yellow solid. $^1$H NMR ($C_6D_6$): 1.62 (m, 2H), 1.79 (m, 2H), 2.62 (b, 1H), 3.05 (b, 1H), 5.20 (m, 1H), 5.94 (m, 1H), 6.05 (m, 1H), 7.70 (m, 2H), 7.81 (m, 2H), 7.87 (m, 2H), 7.99 (m, 1H), 8.72 (m, 1H), 9.79 (m, 1H). HRMS (EI) (M$^+$): calcd. for $C_{24}H_{18}O_2$: 338.13 m/z; Found: 338.13 m/z.

Figure 6:
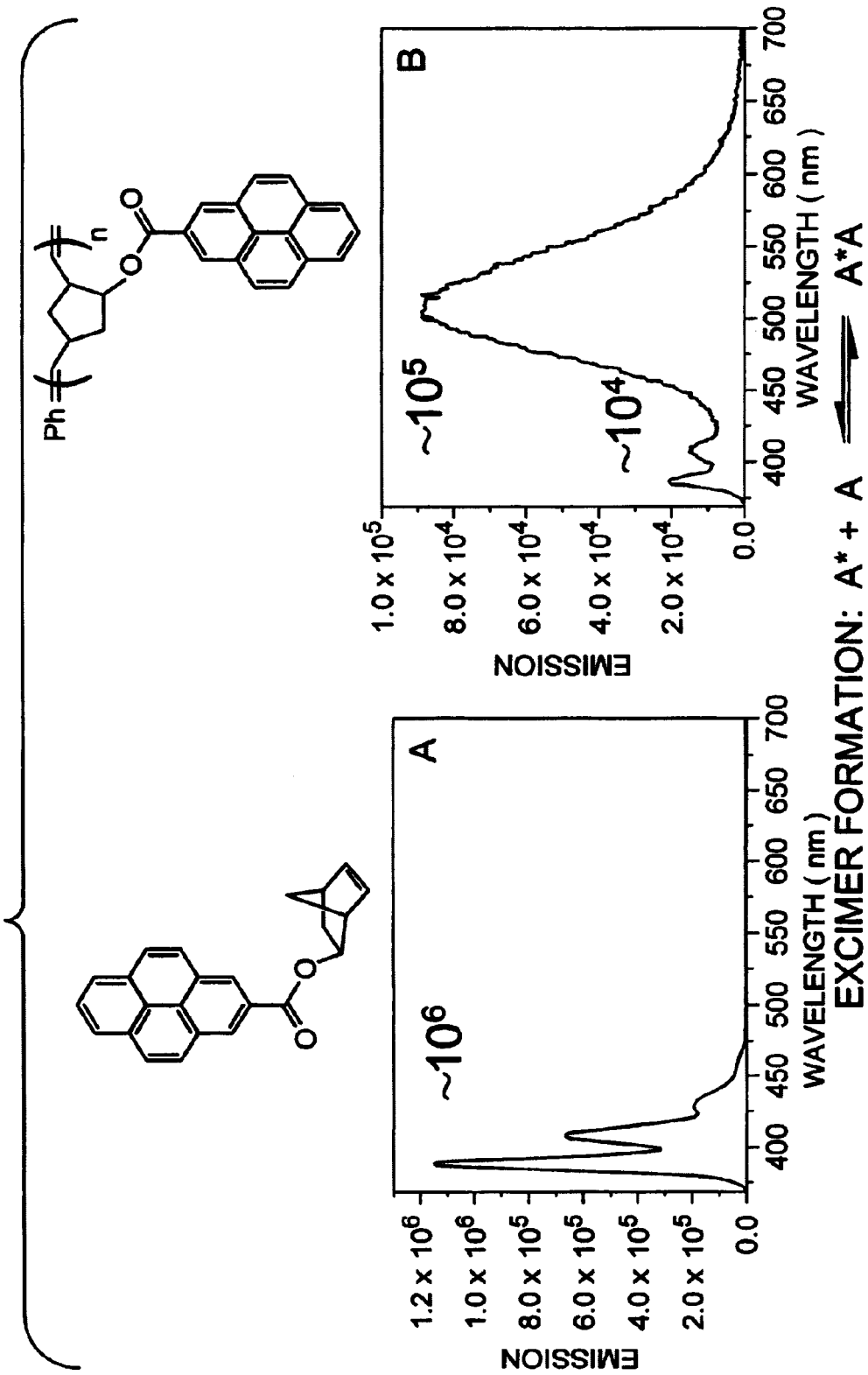
FIG. 6: Graphs of fluorescence emission versus wavelength for monomer 9 (graph A) and GNP-poly 9 (graph B).

Compound 9 is fluorescent, and the fluorescence emission spectra of the monomer and of poly 9 are shown in FIG. 6. As expected, the fluorescence of poly 9 occurs at a lower wavelength, and is broader and less intense, than that of monomer 9 itself. These behaviors suggest the formation of intramolecular excimers in poly 9 due to the close proximity of the chromophores.

Example 7

Figure 8A:
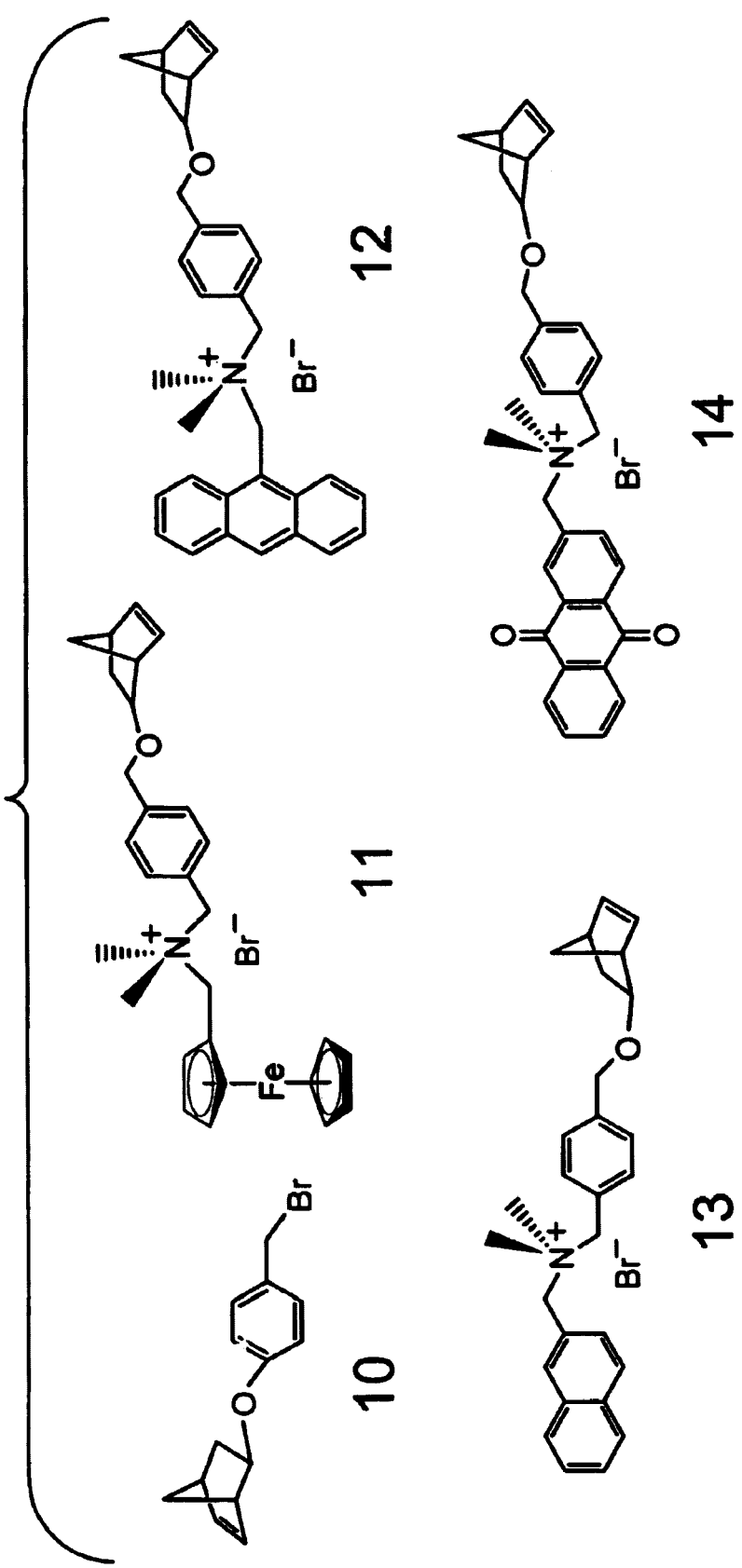
FIGS. 8A–B: Formulas of compounds 10–16.

This example describes the synthesis of α-bromo-α'-(exo-5-norbornene-2-ol)-p-xylene (10) (see FIG. 8A). In an inert atmosphere glovebox, exo-5-norbornene-2-ol (820 mg, 7.44 mmol) was weighed into a 50 mL –Schlenk flask. Dry THF (15 mL) was added and the solution was stirred vigorously while oil-free sodium metal (250 mg, 10.9 mmol) was added. The mixture was then taken out of the glovebox, refluxed for 12 hours under a positive stream of nitrogen, and allowed to cool to room temperature. In a separate 100 mL Schlenk flask, α,α'-dibromo-p-xylene (2.11 g, 8.00 mmol) was dissolved in dry THF (15 mL) and the flask was capped with a pressure-equalizing dropping funnel. The cooled solution of deprotonated exo-5-norbornen-2-ol was then transferred to the pressure-equalizing dropping funnel via cannula filtration and slowly added to the thiophene solution with vigorous stirring over a period of 10 minutes. The dropping funnel was then replaced with a condenser and the mixture was refluxed for an additional 12 hours under a positive stream of nitrogen. Upon cooling to room temperature, the reaction mixture was poured into benzene (50 mL) and washed successively with water (50 mL), 1.0 M NaOH (50 mL), 1.0 M HCl (50 mL), and brine (50 mL). The organic layer was collected, dried over sodium sulfate and filtered into a 500 mL round bottom flask. The solvent was removed on a rotary evaporator. Column chromatography on silica gel with 30% $CH_2Cl_2$ in hexanes as the eluent gave the desired product 10 (1.13 g, 3.87 mmol, 52%) as a clear oil. $^1$HNMR ($C_6D_6$): 1.42 (m, 2H), 1.60 (m, 1H), 1.85 (m, 1H), 2.61 (m, 1H), 2.84 (m, 1H), 3.44 (m, 1H), 3.99 (m, 2H), 4.24 (m, 2H), 5.76 (m, 1H), 6.26 (m, 1H), 7.02 (m, 2H), 7.13 (m, 2H). $^{13}$C NMR ($C_6D_6$): 33.6, 35.2, 41.2, 46.7, 71.1, 80.7, 129.6, 133.7, 137.5, 140.3, 141.2.

Example 8

This example describes the synthesis of N-α-(N,N-dimethylammonium-methylferrocene bromide)-α'-(exo-5-norbornene-2-ol)-p-xylene (11) (see FIG. 8A). In a 100 mL round bottom flask was added 10 (293 mg, 1.00 mmol), anhydrous diethyl ether (25 mL) and a magnetic stirring bar. To this stirring solution of 10 was added a solution of N,N-dimethylaminomethylferrocene (243 mg, 1.00 mmol) in anhydrous diethyl ether (25 mL). The mixture was stirred for 6 hours, during which time a yellow precipitate formed. After this time, a cannula filtration apparatus was used to removed the ether from the flask and the resulting yellow powder was washed with ether (4×50 mL). The solid was dried overnight under vacuum to yield the desired product 11 (391 mg, 0.73 mmol, 73%). $^1$H NMR($D_2O$): $^{13}$C NMR ($CDCl_3$): 34.7, 40.6, 46.2, 46.7, 48.3, 65.8, 66.9, 69.8, 70.7, 70.8, 72.5, 80.9, 126.7, 128.3, 133.2, 133.5, 141.0, 142.0.

Example 9

This example describes a general polymerization procedure for 10 or 11. Polymerization of 11 is described. In an inert atmosphere glovebox, 11 (110 mg, 0.21 mmol) was weighed into a 25 mL round bottom flask equipped with a magnetic stirring bar and dry MeOH (4 mL). To the stirring solution of 11 was added a solution of catalyst 1 (7.0 mg, 0.0085 mmol, 4 mole %) in dry $CH_2Cl_2$ (0.5 mL). The mixture was stirred for 30 minutes, after which time it was removed from the dry box and the polymerization was terminated with ethyl vinyl ether (1 mL). The polymer (ROMP-poly11, 101 mg, 92%) was isolated by pouring the mixture into anhydrous diethyl ether (100 mL) and repeatedly filtering and washing with fresh diethyl ether (4×50 mL).

Example 10

This example describes the synthesis of 12–14 (see FIG. 8A). The synthesis of 12 is representative. A mixture of 10 (440 mg, 1.5 mmol) and 9-NN-dimethylaminomethylanthracene (235 mg, 1.0 mmol) in DMF (25 mL) was refluxed for 16 hours. After this time, the mixture was poured into diethyl ether (250 mL). The yellow solid which precipitated from solution was filtered and washed successively with diethyl ether (4×50 mL) to yield the desired product 12 (432 mg, 0.82 mmol, 82%).

Example 11

Figure 8B:
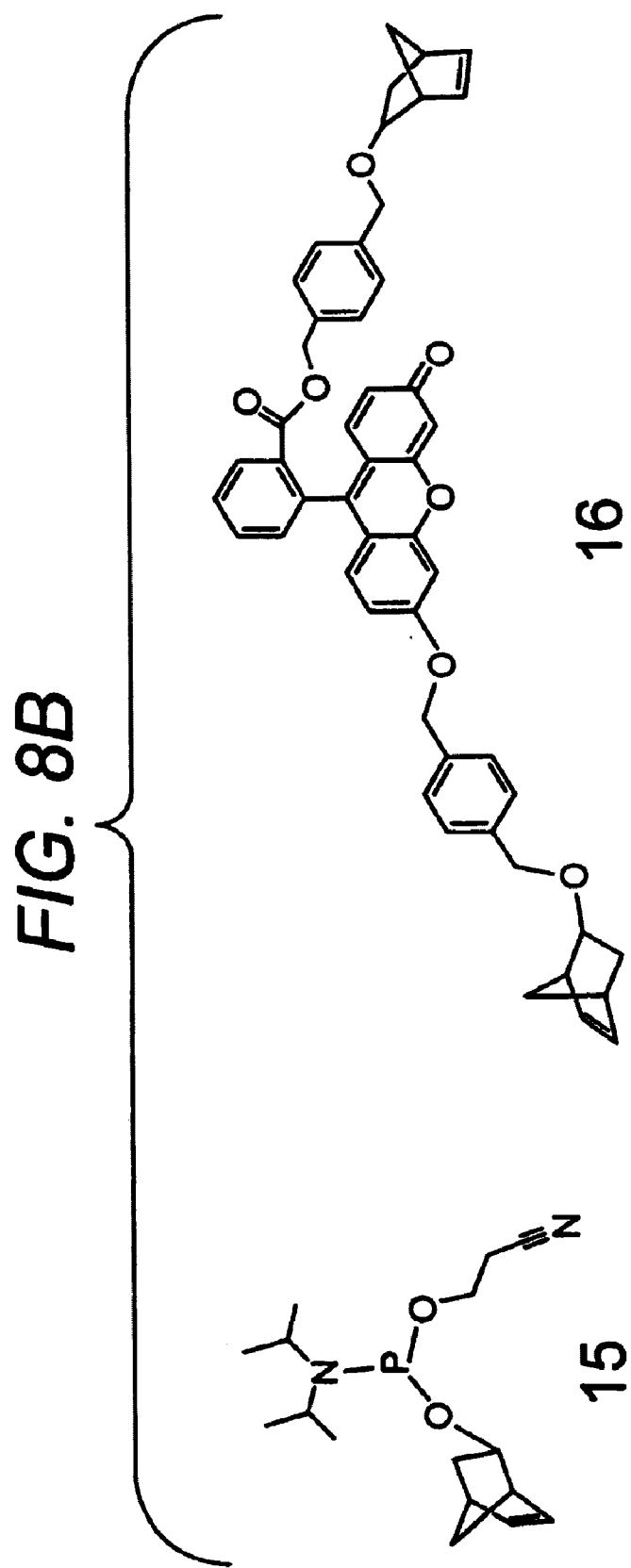

This example describes the synthesis of 15 (see FIG. 8B). A mixture of exo-5-norbornene-2-ol (500 mg, 4.54 mmol), 2-cyanoethyl diisopropylchlorophosphoramidite (1.00 g, 4.22 mmol), and N,N-diisopropylethylamine (0.87 mL, 5.0 mmol) was stirred in dry THF under an atmosphere of nitrogen for a period of 3 hours. After this time, the mixture was poured into a cold solution of 1.0 M NaHCO$_3$ (100 mL) and extracted with CH$_2$Cl$_2$ (3×50 mL). The solvent was removed under vacuum to yield the desired product 15 (1.24 g, 95%).

Example 12

This example describes the synthesis of 16 (see FIG. 8B). A mixture of 10 (1.40 g, 4.77 mmol), fluorescein (800 mg, 2.40 mmol), and potassium carbonate (665 mg, 4.80 mmol) in acetone (25 mL) was refluxed for 36 hours. After this time, the mixture was poured into ice water (100 mL), filtered, and washed with water (400 mL). Recrystalization from DMF with acidic water yielded the desired product 16 (727 mg, 0.96 mmol, 40%).

We claim:

1. A method of preparing nanoparticles having at least one polymer shell attached thereto, said method comprising:
    providing a nanoparticle and initiation monomers, the nanoparticle having a surface;
    attaching the initiation monomers to the surface of the nanoparticle;
    contacting the nanoparticle having the initiation monomers attached thereto with a transition metal ring-opening metathesis catalyst to activate the initiation monomers; and
    contacting the nanoparticle with propagation monomers of the formula P—L—N under conditions effective so that the propagation monomers are polymerized to form at least one polymer shell attached to the nanoparticles,
    wherein:
    N is a cyclic olefin-containing group;
    P is a moiety which gives each polymer shell one or more selected properties; and
    L is a bond or linker whereby N is attached to P.

2. The method of claim 1 wherein the initiation monomers comprise cyclic olefin-containing groups.

3. The method of claim 2 wherein the initiation monomers comprise norbornenyl groups.

4. The method of claim 1 wherein the nanoparticle is a gold nanoparticle.

5. The method of claim 4 wherein the initiation monomers are norbornenyl-containing alkanethiol.

6. The method of claim 5 wherein the initiation monomers are 1-mercapto-10-(exo-5-norbornen-2-oxy)-decane.

7. The method of claim 1 wherein the initiation monomers are mixed with attachment compounds, and both the initiation monomers and the attachment compounds are attached to the surface of the nanoparticle.

8. The method of claim 1 wherein L is a polymer,

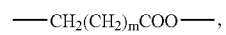

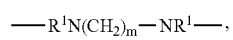

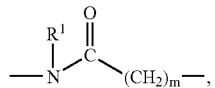

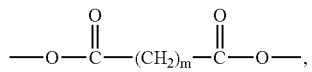

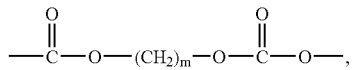

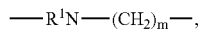

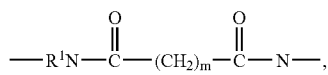

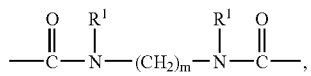

or

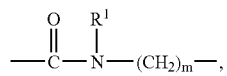

or comprises a moiety B that binds specifically to an analyte; wherein:
$R^1$ has the formula X $(CH_2)m$;
X is —$CH_3$, —$CHCH_3$, —COOH, —$CO_2(CH_2)mCH_3$, —OH, —$CH_2OH$, ethylene glycol, hexa(ethylene glycol), —$O(CH_2)mCH_3$, —$NH_2$, —$NH(CH_2)mNH_2$, halogen, glucose, maltose, fullerene C60, a cyclic olefin, or a nucleic acid; and
m is 0–30.

9. The method of claim 1 wherein N is a norbornenyl-containing group.

10. The method of claim 1 or 9 wherein the catalyst has the formula:

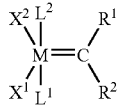

wherein:
M is osmium or ruthenium;
$R^1$ is hydrogen;
$X^1$ and $X^2$, which may be different or the same, are any anionic ligand;
$L^1$ and $L^2$, which may be different or the same, are any neutral electron donor; and
$R^2$ is hydrogen, substituted or unsubstituted alkyl, or substituted or unsubstituted aryl.

11. The method of claim 10 wherein M is ruthenium, $R^1$ is hydrogen, $R^2$ is phenyl, $X^1$ and $X^2$ are both —Cl, and $L^1$ and $L^2$ are both tricyclohexylphosphine.

12. The method of claim 1 or 9 wherein the catalyst has the formula:

[Re($CR^1$($CHR^2$)($R^3$)$R^4$)]n wherein:
Re is rhenium (VII);
$R^1$ is selected from the group consisting of an alkyl having 1–20 carbon atoms, an aryl having 6–20 carbon atoms, an arylalkyl having 7–30 carbon atoms, halogen substituted derivatives of one of the alkyl, aryl, or arylakyl, and silicon-containing analogs of one of the alkyl, aryl, or arylalkyl;
$R^2$ is $R^1$ or is a substituent resulting from the reaction of the Re=$CHR^2$ moiety of the catalyst with an olefin that is being metathesized;
$R^3$ and $R^4$ are ligands which individually or together are sufficiently electron withdrawing to render the rhenium atom electrophilic enough for metathesis reaction; and
n is 1 or more.

13. The method of claim 1 or 9 wherein the catalyst has the formula:

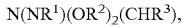

wherein:
M is molybdenum or tungsten;
$R^1$ and $R^2$ each individually may be an alkyl containing 1–20 carbon atoms, an aryl containing 6–20 carbon atoms, an arylalkyl containing 7–20 carbon atoms, a halogen substituted derivative of the alkyl, aryl, or arylalkyl, or a silicon-containing analog of one of the alkyl, aryl, or arylalkyl; and
$R^3$ is an alkyl containing 1–20 carbon atoms, an aryl containing 6–20 carbon atoms, an aralkyl containing 7–20 carbon atoms, or a substituent resulting from the reaction of the M=$CHR^3$ moiety of said catalyst with an olefin being metathesized.

14. The method of claim 1 or 9 wherein the nanoparticle is contacted with propagation monomers under conditions effective so that the monomers are polymerized to form a polymer shell attached to the nanoparticle.

15. The method of claim 14 wherein the polymer shell has redox activity.

16. The method of claim 15 wherein the propagation monomer is exo-5-norbornen-2-yl ferrocenecarboxylate or exo-5-norbornen-2-yl ferroceneacetate.

17. The method of claim 1 or 9 wherein:
the nanoparticle is contacted with a plurality of different propagation monomers under conditions effective so that the monomers are polymerized to form one or more polymer shells attached to the nanoparticle, each polymer shell having one or more selected properties.

18. The method of claim 17 wherein:
the nanoparticle is contacted with first propagation monomers under conditions effective so that the monomers are polymerized to form a first polymer shell attached to the nanoparticles, the first polymer shell having a first selected property; and
then the nanoparticle is contacted with second propagation monomers under conditions effective so that the monomers are polymerized to form a second polymer shell attached to the first polymer shell, the second polymer shell having a second selected property which is different from the first selected property of the first polymer shell.

19. The method of claim 18 wherein one of the polymer shells has redox activity.

20. The method of claim 19 wherein the propagation monomers polymerized to form the shell is exo-5-norbornen-2-yl ferrocenecarboxylate or exo-5-norbornen-2-yl ferroceneacetate.

21. The method of claim 18 wherein the both polymer shells have redox activity.

22. The method of claim 21 wherein the two polymer shells have different redox activities.

23. The method of claim 22 wherein the propagation monomers polymerized to form the first polymer shell is exo-5-norbornen-2-yl ferrocenecarboxylate and the propagation monomers polymerized to form the second polymer shell is exo-5-norbornen-2-yl ferroceneacetate.

24. The method of claim 1 or 9 wherein the polymerization is stopped by adding a compound that terminates polymerization.

25. Nanoparticles comprising one or more polymer shells attached thereto, the polymer shells being formed by polymerizing propagation monomers of the formula P—L—N, wherein:

P is a moiety which provides a desired property or properties to each of the polymer shells;

N is a cyclic olefin-containing group; and

L is a bond or a linker whereby N is attached to P.

26. The nanoparticles of claim 25 wherein L is a polymer,

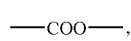

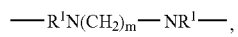

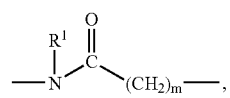

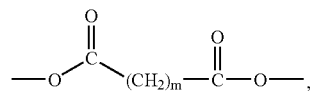

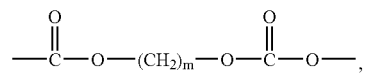

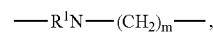

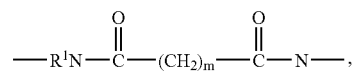

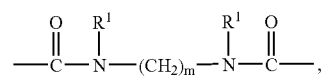

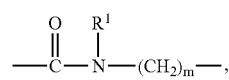

or comprises a binding moiety B that binds specifically to an analyte, wherein:

$R^1$ has the formula $X(CH_2)m$;

X is —$CH_3$, —$CHCH_3$, —COOH, —$CO_2(CH_2)mCH_3$, —OH, —$CH_2OH$, ethylene glycol, hexa(ethylene glycol), —$O(CH_2)mCH_3$, —$NH_2$, —$NH(CH_2)mNH_2$, halogen, glucose, maltose, fullerene C60, a cyclic olefin, or a nucleic acid; and m is 0–30.

27. The nanoparticles of claim 25 wherein N is a norbornenyl-containing group.

28. The nanoparticles of claim 25 or 27 having a single polymer shell attached to them.

29. The nanoparticles of claim 25 or 27 having a plurality of polymer shells attached to them.

30. The nanoparticles of claim 29 having two polymer shells attached to them, the first polymer shell and the second polymer shell having different properties.

31. The nanoparticles of claim 28 wherein the polymer shell has redox activity.

32. The nanoparticles of claim 29 wherein one of the polymer shells has redox activity.

33. The nanoparticles of claim 30 wherein the first polymer shell has redox activity and the second polymer shell has redox activity different than that of the first polymer shell.

34. The nanoparticles of claim 25, 26, or 27 wherein a polymer shell comprises a binding moiety B that binds specifically to an analyte.

35. The nanoparticles of claim 34 wherein the polymer shell comprising the binding moiety B is formed by polymerizing binding monomers of the formula N—L—B, wherein N, L, and B have the same meanings as in claim 34.

36. The nanoparticles of claim 35 wherein the polymer shell comprising the binding moiety B is formed by polymerizing a mixture of binding monomers and one or more propagation monomers.

37. The method of claim 1 wherein the initiation monomers are the same.

38. The method of claim 1 wherein the initiation monomers are different.

39. The method of claim 1 wherein the propagation monomers are the same.

40. The method of claim 1 wherein the propagation monomers are different.

41. The nanoparticles of claim 25 wherein the propagation monomers are the same.

42. The nanoparticles of claim 25 wherein the propagation monomers are different.

43. The nanoparticles of claim 35 wherein the binding monomers are the same.

44. The nanoparticles of claim 35 wherein the binding monomers are different.

* * * * *